US012156888B2

(12) United States Patent
Abate-Daga et al.

(10) Patent No.: US 12,156,888 B2
(45) Date of Patent: *Dec. 3, 2024

(54) CAR T-CELLS FOR THE TREATMENT OF BONE METASTATIC CANCER

(71) Applicant: H. Lee Moffitt Cancer Center and Research Institute, Inc., Tampa, FL (US)

(72) Inventors: Daniel Abate-Daga, Tampa, FL (US); Ismahéne Benzaid, Dijon (FR); Conor C. Lynch, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 930 days.

This patent is subject to a terminal disclaimer.

(21) Appl. No.: 17/265,048

(22) PCT Filed: Aug. 7, 2019

(86) PCT No.: PCT/US2019/045388
§ 371 (c)(1),
(2) Date: Feb. 1, 2021

(87) PCT Pub. No.: WO2020/033464
PCT Pub. Date: Feb. 13, 2020

(65) Prior Publication Data
US 2021/0379108 A1 Dec. 9, 2021

Related U.S. Application Data

(60) Provisional application No. 62/715,504, filed on Aug. 7, 2018.

(51) Int. Cl.
| | | |
|---|---|---|
| A61K 35/17 | (2015.01) | |
| A61K 31/663 | (2006.01) | |
| A61K 31/675 | (2006.01) | |
| A61K 38/00 | (2006.01) | |
| A61K 45/06 | (2006.01) | |
| A61P 35/04 | (2006.01) | |
| C07K 14/705 | (2006.01) | |
| C07K 14/725 | (2006.01) | |
| C07K 16/28 | (2006.01) | |
| C07K 16/30 | (2006.01) | |

(52) U.S. Cl.
CPC ............ *A61K 35/17* (2013.01); *A61K 31/663* (2013.01); *A61K 31/675* (2013.01); *A61K 45/06* (2013.01); *A61P 35/04* (2018.01); *C07K 14/7051* (2013.01); *C07K 14/70521* (2013.01); *C07K 16/2815* (2013.01); *C07K 16/3069* (2013.01); *A61K 38/00* (2013.01)

(58) Field of Classification Search
None
See application file for complete search history.

(56) References Cited

U.S. PATENT DOCUMENTS

| 11,286,306 B2 | 3/2022 | Abate-Daga et al. |
| 2016/0058857 A1 | 3/2016 | Spencer et al. |
| 2016/0175358 A1 | 6/2016 | Jakobovits et al. |
| 2018/0125890 A1 | 5/2018 | Anderson et al. |
| 2018/0319862 A1 | 11/2018 | Thompson et al. |

FOREIGN PATENT DOCUMENTS

| WO | 2018138522 A1 | 8/2018 | |
| WO | 2019064030 A1 | 4/2019 | |
| WO | WO-2019126748 A1 * | 6/2019 | ............. A61K 35/17 |

OTHER PUBLICATIONS

International Search Report issued for PCT/US2019/045388, mailed Nov. 6, 2019.
Harrer et al., RNA-transfection of γ/δ T cells with a chimeric antigen receptor or an α/ß T-cell receptor. a safer alternative to genetically enigneered α/ß T cells for the immunotherapy of melanoma, BMC Caner, 17:551, 2017.
Van der Stegen et al., The pharmacology of second-generation chimeric antigen receptors, Nat Rev Drug Discov. 14 (7), p. 499-509, 2015.
U.S. Appl. No. 17/169,021, Non-Final Office Action issued by USPTO mailed on Feb. 29, 2024.
Gomez-Silva, Diogo, et al., "Tonic 4-1BB Costimulation in Chimeric Antigen Receptors Impedes T Cell Survival and is Vector-Dependent," Cell Reports, vol. 21 (2017), pp. 17-26.
Chen, Xiaoying, et al., "Fusion protein linkers: Property, design and functionality," Advanced Drug Delivery Reviews, vol. 65 (2013), pp. 1357-1369.

* cited by examiner

*Primary Examiner* — Allison M Fox
*Assistant Examiner* — Alyssa G Weston
(74) *Attorney, Agent, or Firm* — Thomas | Horstemeyer, LLP

(57) ABSTRACT

Disclosed herein is a method of providing an anti-cancer immunity in a subject with a bone metastatic cancer. The method involves co-administering to the subject an effective amount of a gamma-delta T cell stimulating agent and an effective amount of a γδ CAR T cell that binds a tumor antigen, such as a prostate antigen for bone metastatic prostate cancer, or a breast cancer antigen for bone metastatic breast cancer. Also disclosed herein is a recombinant T cell that expresses a gamma-delta T cell receptor (TCR) and a chimeric antigen receptor (CAR) polypeptide.

6 Claims, 29 Drawing Sheets

Specification includes a Sequence Listing.

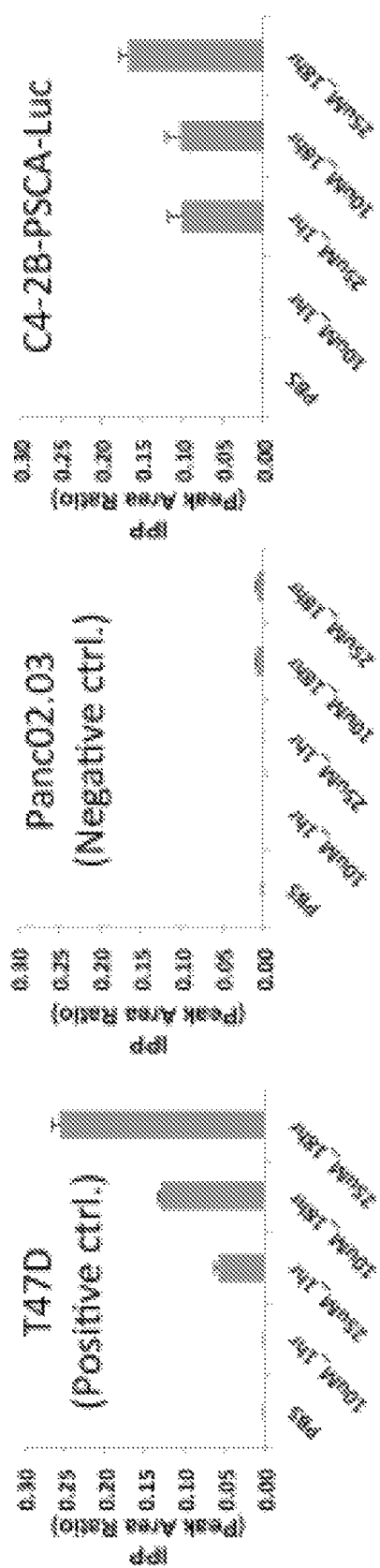

```
SEQUENCE LISTING

<160> NUMBER OF SEQ ID NOS: 5

<210> SEQ ID NO 1
<211> LENGTH: 243
<212> TYPE: PRT
<213> ORGANISM: Artificial Sequence
<220> FEATURE:
<223> OTHER INFORMATION: Synthetic Construct

<400> SEQUENCE: 1

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Gln Arg Arg Lys Tyr Arg Ser Asn Lys Gly Glu Ser Pro
                85                  90                  95

Val Glu Pro Ala Glu Pro Cys His Tyr Ser Cys Pro Arg Glu Glu Glu
            100                 105                 110

Gly Ser Thr Ile Pro Ile Gln Glu Asp Tyr Arg Lys Pro Glu Pro Ala
        115                 120                 125

Cys Ser Pro Arg Val Lys Phe Ser Arg Ser Ala Asp Ala Pro Ala Tyr
    130                 135                 140

Gln Gln Gly Gln Asn Gln Leu Tyr Asn Glu Leu Asn Leu Gly Arg Arg
145                 150                 155                 160

Glu Glu Tyr Asp Val Leu Asp Lys Arg Arg Gly Arg Asp Pro Glu Met
                165                 170                 175

Gly Gly Lys Pro Arg Arg Lys Asn Pro Gln Glu Gly Leu Tyr Asn Glu
            180                 185                 190

Leu Gln Lys Asp Lys Met Ala Glu Ala Tyr Ser Glu Ile Gly Met Lys
        195                 200                 205

Gly Glu Arg Arg Arg Gly Lys Gly His Asp Gly Leu Tyr Gln Gly Leu
    210                 215                 220

Ser Thr Ala Thr Lys Asp Thr Tyr Asp Ala Leu His Met Gln Ala Leu
225                 230                 235                 240
```

Pro Pro Arg

<210> SEQ ID NO 2
<211> LENGTH: 15
<212> TYPE: PRT
<213> ORGANISM: Artificial Sequence
<220> FEATURE:
<223> OTHER INFORMATION: Synthetic Construct

<400> SEQUENCE: 2

```
Arg Glu Glu Glu Gly Ser Thr Ile Pro Ile Gln Glu Asp Tyr Arg
1               5                   10                  15
```

<210> SEQ ID NO 3
<211> LENGTH: 243
<212> TYPE: PRT
<213> ORGANISM: Artificial Sequence
<220> FEATURE:
<223> OTHER INFORMATION: Synthetic Construct

<400> SEQUENCE: 3

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
                20                  25                  30

Arg Pro Glu Ala Cys Arg Pro Ala Ala Gly Gly Ala Val His Thr Arg
            35                  40                  45

Gly Leu Asp Phe Ala Cys Asp Ile Tyr Ile Trp Ala Pro Leu Ala Gly
        50                  55                  60

Thr Cys Gly Val Leu Leu Leu Ser Leu Val Ile Thr Leu Tyr Cys Asn
65                  70                  75                  80

His Arg Asn Gln Arg Arg Lys Tyr Arg Ser Asn Lys Gly Glu Ser Pro
                85                  90                  95

Val Glu Pro Ala Glu Pro Cys His Tyr Ser Cys Pro Gly Gly Gly Gly
            100                 105                 110

Ser Gly Gly Gly Gly Ser Gly Gly Gly Ser Lys Pro Glu Pro Ala
        115                 120                 125

Cys Ser Pro Arg Val Lys Phe Ser Arg Ser Ala Asp Ala Pro Ala Tyr
130                 135                 140

Gln Gln Gly Gln Asn Gln Leu Tyr Asn Glu Leu Asn Leu Gly Arg Arg
145                 150                 155                 160

Glu Glu Tyr Asp Val Leu Asp Lys Arg Gly Arg Asp Pro Glu Met
                165                 170                 175

Gly Gly Lys Pro Arg Arg Lys Asn Pro Gln Glu Gly Leu Tyr Asn Glu
            180                 185                 190

Leu Gln Lys Asp Lys Met Ala Glu Ala Tyr Ser Glu Ile Gly Met Lys
        195                 200                 205

Gly Glu Arg Arg Arg Gly Lys Gly His Asp Gly Leu Tyr Gln Gly Leu
    210                 215                 220

Ser Thr Ala Thr Lys Asp Thr Tyr Asp Ala Leu His Met Gln Ala Leu
225                 230                 235                 240

Pro Pro Arg
```

<210> SEQ ID NO 4
<211> LENGTH: 274
<212> TYPE: PRT
<213> ORGANISM: Artificial Sequence
<220> FEATURE:
<223> OTHER INFORMATION: Synthetic Construct

<400> SEQUENCE: 4

```
Met Val Leu Leu Val Thr Ser Leu Leu Cys Glu Leu Pro His Pro
1               5                   10                  15

Ala Phe Leu Leu Ile Pro Gln Val Gln Leu Gln Glu Ser Gly Pro Gly
                20                  25                  30

Leu Val Lys Pro Ser Gln Thr Leu Ser Leu Thr Cys Thr Val Ser Gly
            35                  40                  45

Gly Ser Ile Ser Ser Gly Gly Tyr Tyr Trp Ile Trp Ile Arg Gln His
        50                  55                  60

Pro Gly Lys Gly Leu Glu Trp Ile Gly Tyr Ile Tyr Tyr Asn Gly Asn
65                  70                  75                  80

Thr Tyr Tyr Asn Pro Ser Leu Lys Ser Arg Val Thr Met Ser Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg Asp Gly Ile Thr Met Ile Arg
        115                 120                 125

Gly Tyr Tyr Tyr Gly Met Asp Val Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Asp Ile Gln Leu Thr Gln Ser Pro Ser Ser Val Ser Ala Ser
                165                 170                 175

Val Gly Asp Arg Val Thr Ile Thr Cys Arg Ala Ser Arg Gly Ile Ser
            180                 185                 190

Ser Trp Leu Ala Trp Tyr Gln Gln Lys Pro Gly Lys Ala Pro Lys Leu
        195                 200                 205

Leu Ile Tyr Thr Ala Ser Ser Leu Gln Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Ala Tyr Ser Phe
                245                 250                 255

Pro Arg Thr Phe Gly Gln Gly Thr Lys Val Glu Ile Lys Ala Ala Ala
            260                 265                 270

Phe Val
```

<210> SEQ ID NO 5
<211> LENGTH: 515
<212> TYPE: PRT
<213> ORGANISM: Artificial Sequence
<220> FEATURE:
<223> OTHER INFORMATION: Synthetic Construct

<400> SEQUENCE: 5

```
Met Val Leu Leu Val Thr Ser Leu Leu Cys Glu Leu Pro His Pro
1               5                   10                  15

Ala Phe Leu Leu Ile Pro Gln Val Gln Leu Gln Glu Ser Gly Pro Gly
                20                  25                  30

Leu Val Lys Pro Ser Gln Thr Leu Ser Leu Thr Cys Thr Val Ser Gly
            35                  40                  45

Gly Ser Ile Ser Ser Gly Gly Tyr Tyr Trp Ile Trp Ile Arg Gln His
        50                  55                  60

Pro Gly Lys Gly Leu Glu Trp Ile Gly Tyr Ile Tyr Tyr Asn Gly Asn
```

-continued

```
             65                  70                  75                  80
    Thr Tyr Tyr Asn Pro Ser Leu Lys Ser Arg Val Thr Met Ser Val Asp
                     85                  90                  95

Thr Ser Lys Asn Gln Phe Ser Leu Lys Leu Ser Ser Val Thr Ala Ala
                    100                 105                 110

Asp Thr Ala Val Tyr Tyr Cys Ala Arg Asp Gly Ile Thr Met Ile Arg
                    115                 120                 125

Gly Tyr Tyr Tyr Gly Met Asp Val Trp Gly Gln Gly Thr Thr Val Thr
                    130                 135                 140

Val Ser Ser Gly Gly Gly Gly Ser Gly Gly Gly Gly Ser Gly Gly Gly
    145                 150                 155                 160

Gly Ser Asp Ile Gln Leu Thr Gln Ser Pro Ser Ser Val Ser Ala Ser
                    165                 170                 175

Val Gly Asp Arg Val Thr Ile Thr Cys Arg Ala Ser Arg Gly Ile Ser
                    180                 185                 190

Ser Trp Leu Ala Trp Tyr Gln Gln Lys Pro Gly Lys Ala Pro Lys Leu
                    195                 200                 205

Leu Ile Tyr Thr Ala Ser Ser Leu Gln Ser Gly Val Pro Ser Arg Phe
                    210                 215                 220

Ser Gly Ser Gly Ser Gly Thr Asp Phe Thr Leu Thr Ile Ser Ser Leu
    225                 230                 235                 240

Gln Pro Glu Asp Phe Ala Thr Tyr Tyr Cys Gln Gln Ala Tyr Ser Phe
                    245                 250                 255

Pro Arg Thr Phe Gly Gln Gly Thr Lys Val Glu Ile Lys Ala Ala Ala
                    260                 265                 270

Phe Val Pro Val Phe Leu Pro Ala Lys Pro Thr Thr Thr Pro Ala Pro
                    275                 280                 285

Arg Pro Pro Thr Pro Ala Pro Thr Ile Ala Ser Gln Pro Leu Ser Leu
                    290                 295                 300

Arg Pro Glu Ala Cys Arg Pro Ala Ala Gly Gly Ala Val His Thr Arg
    305                 310                 315                 320

Gly Leu Asp Phe Ala Cys Asp Ile Tyr Ile Trp Ala Pro Leu Ala Gly
                    325                 330                 335

Thr Cys Gly Val Leu Leu Leu Ser Leu Val Ile Thr Leu Tyr Cys Asn
                    340                 345                 350

His Arg Asn Gln Arg Arg Lys Tyr Arg Ser Asn Lys Gly Glu Ser Pro
                    355                 360                 365

Val Glu Pro Ala Glu Pro Cys His Tyr Ser Cys Pro Arg Glu Glu Glu
    370                 375                 380

Gly Ser Thr Ile Pro Ile Gln Glu Asp Tyr Arg Lys Pro Glu Pro Ala
    385                 390                 395                 400

Cys Ser Pro Arg Val Lys Phe Ser Arg Ser Ala Asp Ala Pro Ala Tyr
                    405                 410                 415

Gln Gln Gly Gln Asn Gln Leu Tyr Asn Glu Leu Asn Leu Gly Arg Arg
                    420                 425                 430

Glu Glu Tyr Asp Val Leu Asp Lys Arg Arg Gly Arg Asp Pro Glu Met
                    435                 440                 445

Gly Gly Lys Pro Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
    465                 470                 475                 480

Gly Glu Arg Arg Arg Gly Lys Gly His Asp Gly Leu Tyr Gln Gly Leu
                    485                 490                 495
```

```
Ser Thr Ala Thr Lys Asp Thr Tyr Asp Ala Leu His Met Gln Ala Leu
        500                 505                 510

Pro Pro Arg
        515
```

CAR T-CELLS FOR THE TREATMENT OF BONE METASTATIC CANCER

CROSS-REFERENCE TO RELATED APPLICATIONS

This application is a National Stage of International Application No. PCT/US2019/045388, filed Aug. 7, 2019, which claims benefit of U.S. Provisional Application No. 62/715,504, filed Aug. 7, 2018, which is hereby incorporated herein by reference

SEQUENCE LISTING

This application contains a sequence listing filed in electronic form as an ASCII.txt file entitled "320803_2260_Sequence_Listing_ST25" created on Aug. 6, 2019. The content of the sequence listing is incorporated herein in its entirety.

BACKGROUND

Prostate cancer frequently metastasizes to the skeleton. Of the 31,620 men expected to succumb to disease in 2019, 90% will have evidence of bone metastases. The lesions are currently incurable and are of huge clinical importance and expense. In bone, metastatic prostate cancer cells cause bone destruction/osteolysis but are hallmarked by areas of extensive osteogenesis that contribute to disease associated morbidity and mortality. Recent advances with second generation androgen deprivation therapies, radium-223, and bisphosphonates have improved overall survival and mitigated cancer induced bone disease. However, the disease typically progresses within 2-3 years underscoring the urgent clinical need for new therapies.

SUMMARY

Disclosed herein is a method of providing an anti-cancer immunity in a subject with a bone metastatic cancer, such as bone metastatic prostate cancer, bone metastatic breast cancer, or primary tumors that localize to the bone, such as myeloma. The method involves co-administering to the subject an effective amount of a gamma-delta T cell stimulating agent and an effective amount of a γδ CAR T cell that binds a tumor antigen, such as a prostate antigen for bone metastatic prostate cancer, or a breast cancer antigen for bone metastatic breast cancer. The CAR T cell therefore is a T cell expressing both a gamma-delta T cell receptor (TCR) and chimeric antigen receptor (CAR) polypeptide, wherein the CAR comprises a tumor antigen binding domain, a transmembrane domain, an intracellular signaling domain, and a co-stimulatory signaling region.

Also disclosed herein is a recombinant T cell that expresses a gamma-delta T cell receptor (TCR) and a chimeric antigen receptor (CAR) polypeptide, wherein the CAR comprises a tumor antigen binding domain, a transmembrane domain, an intracellular signaling domain, and a co-stimulatory signaling region.

In some embodiments, the gamma-delta T cell stimulating agent comprises a bisphosphonate. For example, the bisphosphonate can be selected from the group comprising alendronate, clodronate, etidronate, pamidronate, tiludronate, ibandronate, zoledronate, olpadronate, residronate and neridronate.

In some embodiments, the tumor antigen is a prostate cancer antigen, such as prostate stem cell antigen (PSCA). In some embodiments, the tumor antigen is a breast cancer antigen, such as chondroitin sulfate proteoglycan-4 (CSPG4). The tumor antigen binding domain is in some embodiments an antibody fragment that specifically binds the tumor antigen. For example, the antigen binding domain can be a Fab or a single-chain variable fragment (scFv) of an antibody that specifically binds PSCA. The tumor antigen binding domain is in some embodiments an aptamer that specifically binds the tumor antigen. For example, the tumor antigen binding domain can be a peptide aptamer selected from a random sequence pool based on its ability to bind the tumor antigen. The tumor antigen binding domain can also be a natural ligand of the tumor antigen, or a variant and/or fragment thereof capable of binding the tumor antigen. For example, antibodies, including scFvs, that selectively bind PSCA are described in U.S. Pat. No. 7,595,379, which is incorporated by reference for the use and sequences of these antibodies to make scFvs for use in the disclosed CAR polypeptides.

In some embodiments, the CAR polypeptide is defined by the formula:

SP-TA-HG-TM-CSR-ISD; or

SP-TA-HG-TM-ISD-CSR wherein "SP" represents a signal peptide,
wherein "TA" represents a tumor antigen binding domain,
wherein "HG" represents and optional hinge domain,
wherein "TM" represents a transmembrane domain,
wherein "CSR" represents a co-stimulatory signaling region,
wherein "ISD" represents an intracellular signaling domain, and
wherein "-" represents a bivalent linker.

In some of these embodiments, the costimulatory signaling region comprises the cytoplasmic domain of a CD28. In some of these embodiments, the hinge domain comprises a CD8 hinge domain. In some of these embodiments, the transmembrane domain transmembrane a CD8 hinge domain.

In some embodiments, the costimulatory signaling region comprises a mutated or deleted TRAF-binding domain. For example, the CAR can comprise a CD27 co-stimulatory domain (e.g. CD27Z) where the TRAF-binding site has been replaced with a flexible linker. The following is the amino acid sequence of CD27Z:

(SEQ ID NO: 1)
FVPVFLPAKPTTTPAPRPPTPAPTIASQPLSLRPEACRPAAGGAVHTRGL

DFACDIYIWAPLAGTCGVLLLSLVITLYCNHRNQRRKYRSNKGESPVEPA

EPCHYSCPREEEGSTIPIQEDYRKPEPACSPRVKFSRSADAPAYQQGQNQ

LYNELNLGRREEYDVLDKRRGRDPEMGGKPRRKNPQEGLYNELQKDKMAE

AYSEIGMKGERRRGKGHDGLYQGLSTATKDTYDALHMQALPPR.

The TRAF-binding site has the amino acid sequence REEEGSTIPIQEDYR (SEQ ID NO:2). In the following sequence (TRAF-mut CD27Z), the TRAF-binding site has been replaced with a flexible linker:

(SEQ ID NO: 3)
FVPVFLPAKPTTTPAPRPPTPAPTIASQPLSLRPEACRPAAGGAVHTRGL

DFACDIYIWAPLAGTCGVLLLSLVITLYCNHRNQRRKYRSNKGESPVEPA

-continued

EPCHYSCPGGGGSGGGGSGGGGSKPEPACSPRVKFSRSADAPAYQQGQNQ

LYNELNLNLGRREEYDVLDKRRGRDPEMGGKPRRKNPQEGLYNELQKDKMAE

AYSEIGMKGERRRGKGHDGLYQGLSTATKDTYDALHMQALPPR.

In some embodiments, the scFv is an anti-PSCA scFv having the amino acid sequence:

(SEQ ID NO: 4)
MVLLVTSLLLCELPHPAFLLIPQVQLQESGPGLVKPSQTLSLTCTVSGGS

ISSGGYYWIWIRQHPGKGLEWIGYIYYNGNTYYNPSLKSRVTMSVDTSKN

QFSLKLSSVTAADTAVYYCARDGITMIRGYYYGMDVWGQGTTVTVSSGGG

GSGGGGSGGGGSDIQLTQSPSSVSASVGDRVTITCRASRGISSWLAVVYQ

QKPGKAPKLLIYTASSLQSGVPSRFSGSGSGTDFTLTISSLQPEDFATYY

CQQAYSFPRTFGQGTKVEIKAAAFV.

Therefore, in some embodiments, the CAR polypeptide has the amino acid sequence:

(SEQ ID NO: 5)
MVLLVTSLLLCELPHPAFLLIPQVQLQESGPGLVKPSQTLSLTCTVSGGS

ISSGGYYWIWIRQHPGKGLEWIGYIYYNGNTYYNPSLKSRVTMSVDTSKN

QFSLKLSSVTAADTAVYYCARDGITMIRGYYYGMDVWGQGTTVTVSSGGG

GSGGGGSGGGGSDIQLTQSPSSVSASVGDRVTITCRASRGISSWLAVVYQ

QKPGKAPKLLIYTASSLQSGVPSRFSGSGSGTDFTLTISSLQPEDFATYY

CQQAYSFPRTFGQGTKVEIKAAAFVPVFLPAKPTTTPAPRPPTPAPTIAS

QPLSLRPEACRPAAGGAVHTRGLDFACDIYIWAPLAGTCGVLLLSLVITL

YCNHRNQRRKYRSNKGESPVEPAEPCHYSCPREEEGSTIPIQEDYRKPEP

ACSPRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTA

TKDTYDALHMQALPPR.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A to 2C show IPP production in response to zoledronate. Following treatment of tumor cells with ZOL, IPP was measured in cell extracts by tandem LC-MS/MS, using AppCp as an internal standard. FIG. 2A shows T47D cells used as a positive control. FIG. 2B shows Panc02.03 used as negative control. FIG. 2C shows results for C4-2B-PSCA-Luc cells. ZOL treatment was administered for 1 h or 18 h, at 2 different doses: 10 μM or 25 μM.

FIG. 3A shows expression of CD27 and IL2RB (CD122) on αβ T-cells expressing anti-PSCA CARs with different endodomains. FIG. 3B shows comparison of CAR expression in αβ vs. γδ T-cells from the same donor. FIG. 3C shows effect of CAR hinge/transmembrane region (CD8- vs. CD28-derived) on phenotype γδ CAR-T cells. FIG. 3D shows in vitro growth of Untransduced (UT) and CAR-transduced γδ T-cells (mean+/−SD). *OKT3 stimulated PBMC, transduced twice with the indicated retroviral vector. Gated on lymphoid, single, viable, CD3+, αβ v cells. #ZOL-stimulated PBMC, transduced twice with the indicated retroviral vector. Gated on lymphoid, single, viable, CD3+, Vdelta2+ cells.

FIG. 4A is a schematic representation of the strategy. CAR- or mock-transduced αβ or γδ T-cells are incubated with Protein-L beads (circles), which bind the CAR ectodomain. After magnetic pull-down of complexes, LC-MS/MS is used for identification of proteins that communoprecipitate with CARs. FIG. 4B are example results obtained for a comparison of 2 variations of the anti-PSCA CAR, expressed in 4 T-cells. Graph represents the fold change (log-transformed) of the abundance of each protein in CAR-T vs. GFP T-cells. X-axis represents the abundance normalized by the size of the protein. FIG. 4C is a Western blot of whole-cell extract and CAR-immunocomplex showing coimmunoprecipitation a lower molecular weight CD3 protein. FIG. 4D is a schematic representation of interactome analysis for the comparison of 4 vs. γδ CAR-T interaction partners.

FIGS. 7A and 7B show tumor cells without ZOL pretreatment. FIGS. 6C and 6D show tumor cells with 2 h ZOL pretreatment. FIGS. 6A and 6C show tumor cell viability 2 h post co-culture. FIGS. 6B and 6D show 30 h post co-culture.

FIGS. 7A to 7D show C4-2B cells inoculated into NSG mice and treated with either zoledronate (ZOL) or vehicle control. After establishment and randomization mice (n=15/group) were inoculated with $3.5 \times 10^6$ αβT-cells. Subsets of mice were removed from the study at 1, 3 and 5 days late. FIG. 7A shows flow cytometry results from tibias isolated, flushed and assessed for human CD3 Vd2 positivity as a readout for the presence of γδ T-cells. Number illustrate the percentage of γδ T-cells in the total marrow analysis over time. FIG. 7B shows example tumor growth measured over the course of 7 days using bioluminescence as a correlate of tumor growth. FIG. 7C is a graph showing RLUs quantitated over time and the growth rates calculated for each group. Asterisk indicates statistical significance. Mice at the final time point were assessed for γδ T-cell localization (CD3), apoptosis (cleaved caspase-3; CC3) and proliferation (phospho histone H3; pHH3). FIG. 7D shows immunostaining with pan cytokeratin to localize prostate cancer cells. Arrows indicate positivity. DAPI was used as a nuclear counterstain.

FIG. 12A shows trichrome and hematoxylin histological analysis showing bone and tumor areas in tibia tissue sections. FIG. 10B shows 3D reconstructions of trabecular bone volume from high resolution μCT scanning. FIG. 10C shows quantification of μCT-based analysis of bone architecture. Significantly greater bone volume and trabecular thickness was observed in tibias from animals treated with γδ CAR-T cells. FIG. 10D shows faxitron X-ray analysis showing significant mitigation of cancer-induced osteolysis in animals treated with γδ CAR-T cells.

FIG. 14A shows RTCA analysis of C4-2B-PSCA cells treated with untransduced (UT) γδ T cells or anti-PSCA γδ CAR-T cells, +/−MSC CM. Detail of initial 12 h in upper left corner. FIG. 14B shows quantification of area under the curve (AUC) of the RTCA analysis shown in FIG. 14A.

DETAILED DESCRIPTION

Figure 1:
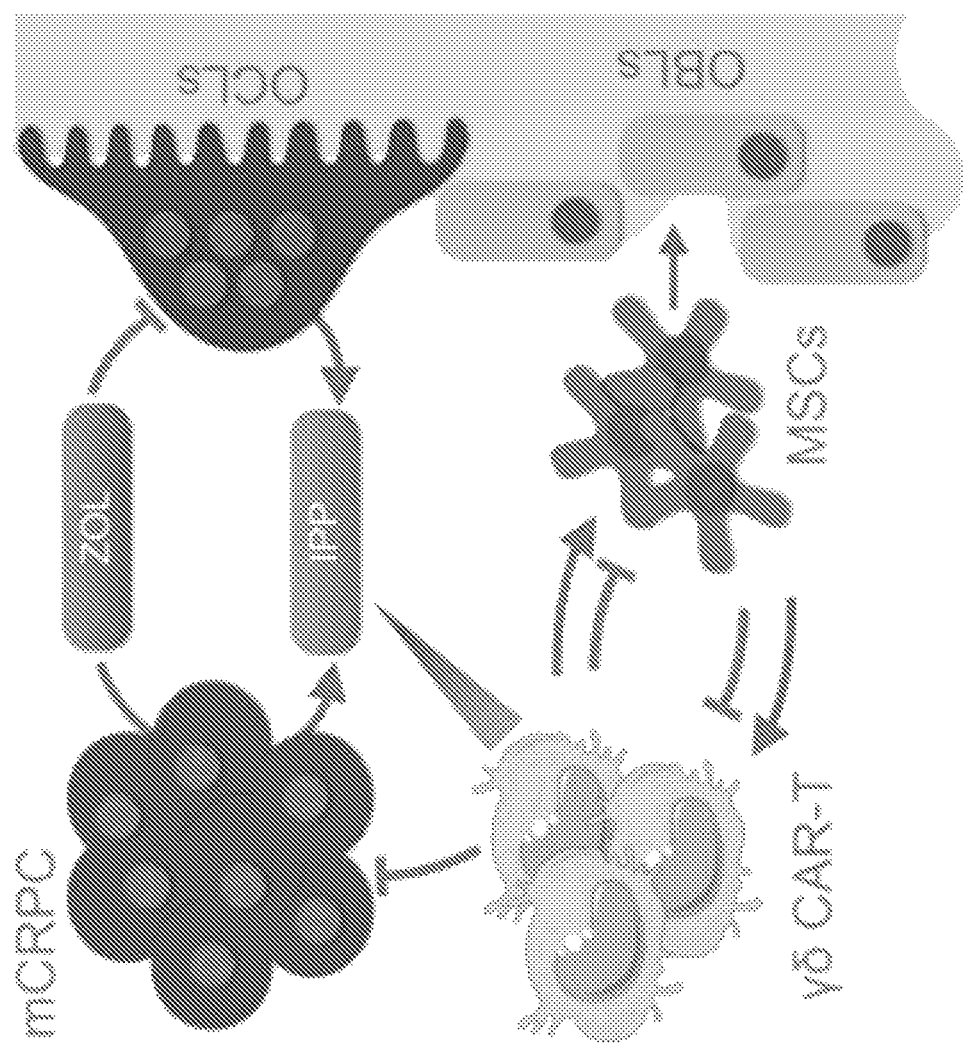
FIG. 1 is a schematic illustrating an embodiment of the disclosed method for treating bone metastatic prostate cancer cells. γδ CAR-T recognize and eliminate PSCA expressing bone metastatic CRPC cells. Zoledronate treatment of bone metastatic CRPC in vivo promote osteoclast apoptosis and leads to the accumulation of IPP generated by the tumor cells. IPP drives the recruitment and enhances the anticancer activity of adoptively transferred γδ CAR-T cells. Also depicted are reciprocal effects of the bone stroma on γδ CAR-T activity.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "protein domain" refers to a portion of a protein, portions of a protein, or an entire protein showing structural integrity; this determination may be based on amino acid composition of a portion of a protein, portions of a protein, or the entire protein.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics.

Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

System for Treatment of Bone Metastatic Prostate Cancer

Disclosed herein is a method of providing an anti-cancer immunity in a subject with a bone metastatic prostate cancer. The method involves co-administering to the subject an effective amount of a gamma-delta (γδ) T cell stimulating agent and an effective amount of a γδ CAR T cell that binds a tumor antigen, such as a prostate cancer antigen, a breast cancer antigen, or a myeloma antigen. The CAR T cell therefore is a T cell expressing both a γδ T cell receptor (TCR) and chimeric antigen receptor (CAR) polypeptide, wherein the CAR comprises a tumor antigen binding domain, a transmembrane domain, an intracellular signaling domain, and a co-stimulatory signaling region.

γδ T Cell Stimulating Agents

The γδ T cell stimulating agent may be selected from, for example, isopentenyl pyrophosphate (IPP); analogs of IPP such as bromohydrin pyrophosphate and (E)-4-Hydroxy-3-methylbut-2-enyl pyrophosphate; and inhibitors of farnesyl pyrophosphate synthase (FPPS) such as bisphosphonates.

Bisphosphonates constitute a class of drugs for use in a variety of diseases of bone and calcium metabolism. Bisphosphonates are synthetic analogs of pyrophosphates characterized by phosphorus-carbon-phosphorus backbone that renders them resistant to hydrolysis. The properties of the bisphosphonates vary based on different substitutions at the carbon atom of the phosphorus-carbon-phosphorus backbone. A group of currently known bisphosphonates include alendronate, clodronate, etidronate, pamidronate, tiludronate, ibandronate, zoledronate, olpadronate, residronate and neridronate.

γδ CAR T Cells

T-cells are divided into two groups based on their T-Cell Receptor (TCR) components. The TCR heterodimer consists of an α and β chain in 95% of T cells. These recognize foreign antigens via peptides presented by MHC molecules on antigen presenting cells and are essential for adaptive immunity. 5% of T cells have TCRs consisting of γ and δ chains. γδ TCRs are MHC independent and detect markers of cellular stress expressed by tumors.

γδ T cells recognize pathogens and transformed cells in an HLA-unrestricted manner. They respond to markers of cellular stress (e.g. phosphoantigens released by transformed cells as by-products of the mevalonate biosynthetic pathway). γδ T cells display both innate cytotoxic functions and antigen-presenting capability, particularly in the presence of antibody-opsonized target cells.

γδ T-cells are responsible for "lymphoid stress surveillance," i.e., sensing and responding immediately to infections or non-microbial stress without the need of clonal expansion or de novo differentiation.

The activation of γδ T cells is regulated by a balance between stimulatory and inhibitory signals. They are activated by γδ TCR ligands (e.g. phosphoantigens) in combination with MHC-associated ligands of the activatory receptor killer cell lectin-like receptor subfamily K, member 1 (KLRK1), also known as NKG2D, such as MHC class I polypeptide-related sequence A (MICA), MICB, and various members of the UL16-binding protein (ULBP) family.

In some embodiments, a γδ CAR T cell will only be fully activated and capable of killing a target cell which expresses a first antigen which is capable of binding to the γδ TCR and a second antigen which is capable of binding to the CAR. By way of example, a γδ TCR may recognize phosphoantigens (e.g. Isopentenyl pyrophosphate (IPP), Bromohydrin Pyrophosphate (BrHPP) and (E)-4-Hydroxy-3-methyl-but-2-enyl pyrophosphate (HMBPP)); major histocompatibility complex class I chain-related A (MICA); major histocompatibility complex class I chain-related B (MICB); NKG2D ligand 1-6 (ULBP 1-6); CD1c; CD1d; endothelial protein C receptor (EPCR); lipohexapeptides; phycoreythrin or histidyl-tRNA-synthase.

The disclosed system involves the use of γδ T cells that are engineered to express the disclosed CARs (also referred to herein as "γδ CAR T cells"). These cells are preferably obtained from the subject to be treated (i.e. are autologous). However, in some embodiments, cell lines or donor effector cells (allogeneic) are used.

Methods for obtaining and enriching γδ T cells are known in the art and can be used in the present methods. For example, the method can involve stimulating a mixture of T cells with a γδ T cell stimulating agent. As used herein, a "γδ T cell stimulating agent" refers to any agent which selectively stimulates the proliferation and/or survival of γδ T cells from a mixed starting population of cells. The resulting cell population is enriched with an increased number of γδ T cells. This can be achieved by stimulating fresh peripheral blood mononuclear cells (PBMC) with culture medium supplemented with zoledronate (or other amino-bisphosphonates). Retroviral transduction can be performed between days 5-7 post-stimulation, following standard protocols.

Chimeric Antigen Receptors (CARs)

The isolated γδ T cells can then be engineered to express a CAR that selectively binds a prostate antigen. The disclosed CAR is generally made up of three domains: an ectodomain, a transmembrane domain, and an endodomain. The ectodomain comprises the TAA-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an intracellular signaling domain (ISD) and a co-stimulatory signaling region (CSR).

In some embodiments, the TAA-binding region is single chain variable fragment (scFv) antibody that binds a prostate antigen. The affinity/specificity of a scFv is driven in large part by specific sequences within complementarity determining regions (CDRs) in the heavy (VH) and light (VL) chain. Each VH and VL sequence will have three CDRs (CDR1, CDR2, CDR3).

In some embodiments, the prostate antigen is PSA, PSM, PCTA, or PSCA. In particular embodiments, the prostate antigen is PSCA. Antibodies that specifically bind PSCA are known and described, for example, in U.S. Pat. No. 7,595,379, which is incorporated by reference for the use and sequences of these antibodies to make scFvs for use in the disclosed CAR polypeptides.

In some embodiments, the disclosed CAR is defined by the formula:

SP-TA-HG-TM-CSR-ISD;

wherein "SP" represents an optional signal peptide,
wherein "TA" represents a tumor antigen binding domain,
wherein "HG" represents an optional hinge domain,
wherein "TM" represents a transmembrane domain,
wherein "CSR" represents the co-stimulatory signaling region,
wherein "ISD" represents an intracellular signaling domain, and
wherein "-" represents a peptide bond or linker.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3 domain. TanCAR T cell activation is achieved only when target cells co-express both targets.

A dual CAR T cell expresses two separate CARs with different ligand binding targets; one CAR includes only the CD3 domain and the other CAR includes only the co-stimulatory domain(s). Dual CAR T cell activation requires co-expression of both targets on the tumor.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

In some cases, the anti-PSCA binding agent is an affinity maturated scFv. In some cases, the anti-PSCA has a dissociation constant (Ko) for the TAA that is less than 50 nM, 40 nM, 30 nM, 25 nM, 20 nM, 15 nM, or 10 nM.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIy, FcγRIIIγ, FcεRIβ (FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

In some embodiments, the anti-PSCA binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Nucleic Acids and Vectors

Also disclosed are polynucleotides and polynucleotide vectors encoding the disclosed CARs that allow expression of the CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc (Birmingham, Ala.).

Therapeutic Methods

The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to the tumor antigen.

Adoptive transfer of immune effector cells expressing chimeric antigen receptors is a promising anti-cancer therapeutic. Following the collection of a patient's immune effector cells, the cells may be genetically engineered to express the disclosed CARs, then infused back into the patient.

The disclosed γδ CAR T cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The cancer of the disclosed methods can be any prostate cancer that has metastasized to another tissue, such as bone.

The disclosed γδ CAR T cells can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed γδ CAR T cells can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MED14736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed γδ CAR T cells can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec ST1571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with γδ CAR T cells may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)– negative chemokines such as IP-10, MCP-3, MIG, and SDF-la from the human CXC and C—C chemokine families. Suitable cytokines include cytokine derivatives, cytokine variants, cytokine fragments, and cytokine fusion proteins.

In some embodiments, a therapeutic agent for use in combination with γδ CAR T cells may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with γδ CAR T cells may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed γδ CAR T cells are administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed γδ CAR T cells are administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines as cancer therapies are being investigated both pre-clinically and clinically, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-β (Dranoff 2004). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon 2011). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TI Ls (tumor infiltrating lymphocytes). While PD1-PDL1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-β receptor are resistant to the immunosuppression by lymphoma secreted TGF-β. These transduced cells showed notably increased antitumor activity in vivo when compared to their control counterparts.

Tandem and dual CAR-T cells are unique in that they possess two distinct antigen binding domains. A tandem CAR contains two sequential antigen binding domains facing the extracellular environment connected to the intracellular costimulatory and stimulatory domains. A dual CAR is engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC tag, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a tumor related antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tumor tissue, and is advantageous in situations where certain normal tissues may express very low levels of a tumor associated antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

In some embodiments, two or more of these engineered features may be combined to create an enhanced, multifunctional CAR-T. For example, it is possible to create a CAR-T cell with either dual- or conditional-CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Several different methods for CAR expression may be used including retroviral transduction (including γ-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

A number of embodiments of the invention have been described.

Nevertheless, it will be understood that various modifications may be made without departing from the spirit and scope of the invention. Accordingly, other embodiments are within the scope of the following claims.

EXAMPLES

Example 1

As disclosed herein, systemic administration of anti-PSCA γδ CAR-T Cells, in combination with zoledronate results in accumulation of IPP in prostate cancer cells and osteoclasts. Secretion of part of that IPP leads to recruitment of γδ CAR-T cells to the disease sites and, once there, they recognize prostate cancer cells through two independent mechanisms: PSCA recognition by CAR, and IPP recognition through the γδ TCR. As a result, a localized, effective anti-tumor response is achieved. There are also reciprocal effects between γδ T-cells and the bone stroma namely, MSCs (FIG. 1). This disclosed system capitalizes on the availability of an FDA-approved pharmacological agent, zoledronate, which is routinely administered to patients with bone metastatic prostate cancer. In order to verify that zoledronate effectively induces IPP accumulation in a model system, C4-2B-PSCA-Luc human CRPC prostate cancer cells were treated with 10 µM or 25 µM of zoledronate, for 1 h or 18 h. Intracellular IPP levels were measured using a semi-quantitative mass spectrometry assay. T47D breast cancer cells were used as positive control, and Panc02.03 pancreatic cancer cells were used as negative controls. IPP levels were detectable over background, in T47D cells, after 1 h of treatment with high-dose zoledronate; and at both doses following 18 h of treatment (FIG. 2A). Panc02.03 cells did not produce IPP, even after prolonged treatment with high doses of zoledronate (FIG. 2B). C4-2B-PSCA-Luc cells, in turn, produced high levels of IPP in response to zoledronate, following a pattern similar to that of T47D cells (FIG. 2C).

Figure 3A:
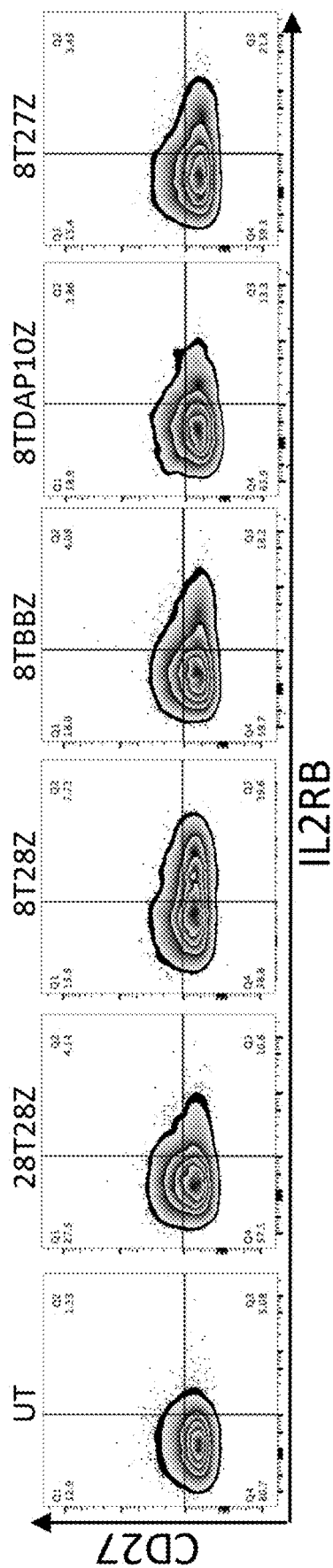
FIG. 3A to 3D show impact of CAR endodomain on T-cell biology.

In order to maximize the synergism between PSCA and phosphoantigen recognition, the optimal CAR design was explored. As a first attempt, multiple variations of an anti-PSCA CAR were generated, differing in the choice of costimulatory moiety and/or hinge/transmembrane domain. The combination of these elements is indicated in the nomenclature of the CARs. For instance, an 8T28Z CAR has a CD8-derived hinge/transmembrane domain (hence the '8T'), and a CD28-derived costimulation domain followed by a CD3-derived activation domain (hence the '28Z'). The guiding principles for the design of CARs have evolved over the years. One of the key modifications, introduced to the original first-generation CAR, was the incorporation of a costimulatory domain, allowing for enhanced in vivo persistence and therapeutic success. While most CARs tested in the clinic employ either a CD28- or 4-1BB-derived costimulation module, the optimization of these modules is an area of active research. Upon CAR ligation, the type of costimulation chosen may impact T cell biology at multiple levels, including cytokine production and metabolic skewing. Moreover, in the absence of CAR stimulation, the type of costimulation can condition the behavior of T cells, by modulating the effects of tonic signaling, and by altering the expression of the cytokine receptor. As shown, the mere expression of a CAR in $\alpha\beta$ T-cells was sufficient to increase the surface expression of the beta subunit of the IL-2 receptor (IL2RB, CD122; FIG. 3A). When CARs containing either CD28, 4-1BB, DAP10, or CD27 costimulation were compared, this effect was most prominent in those containing CD28. Furthermore, there were differences between 2 CD28-based CARs that differed only in their structural hinge/transmembrane domain (8T28Z vs. 28T28Z).

Figure 3B:
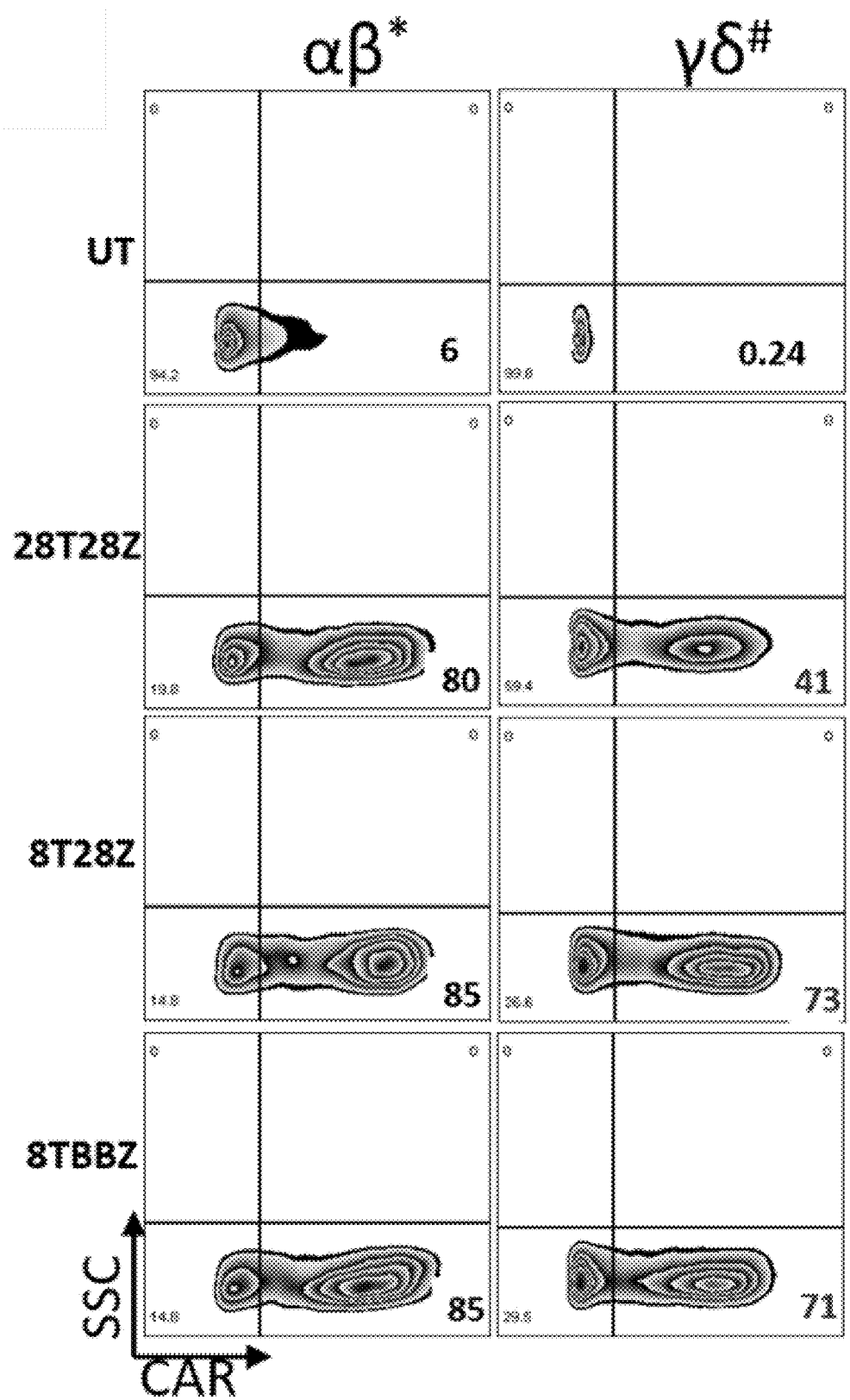
Figure 3C:
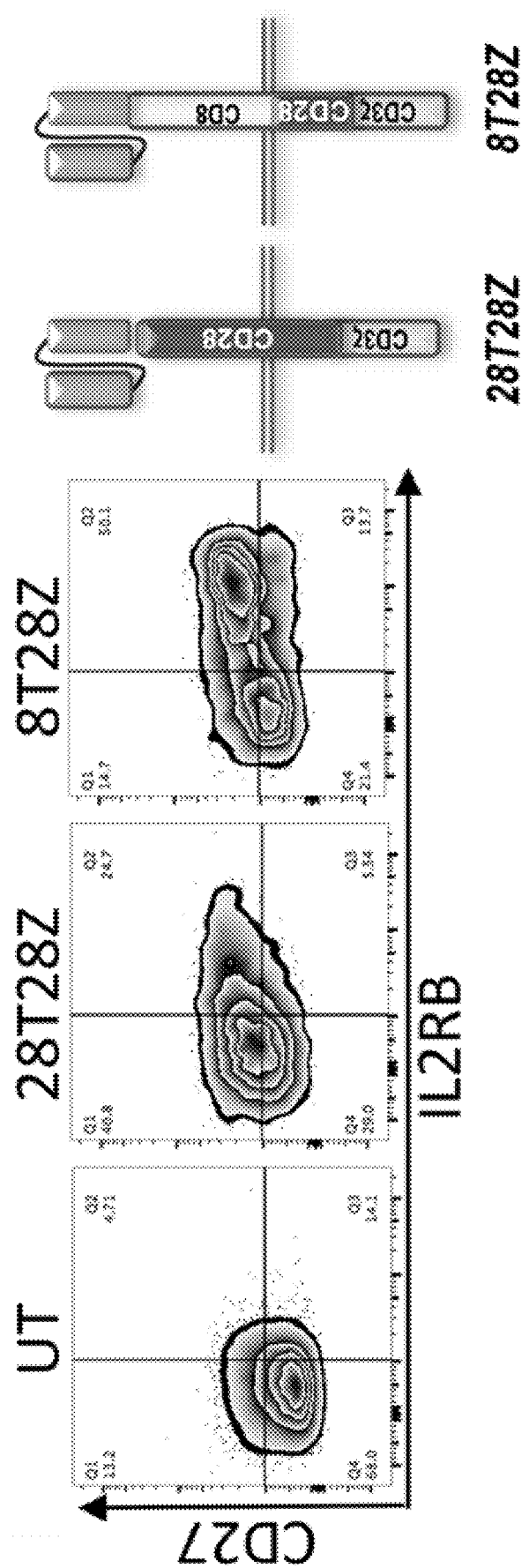
Figure 3D:
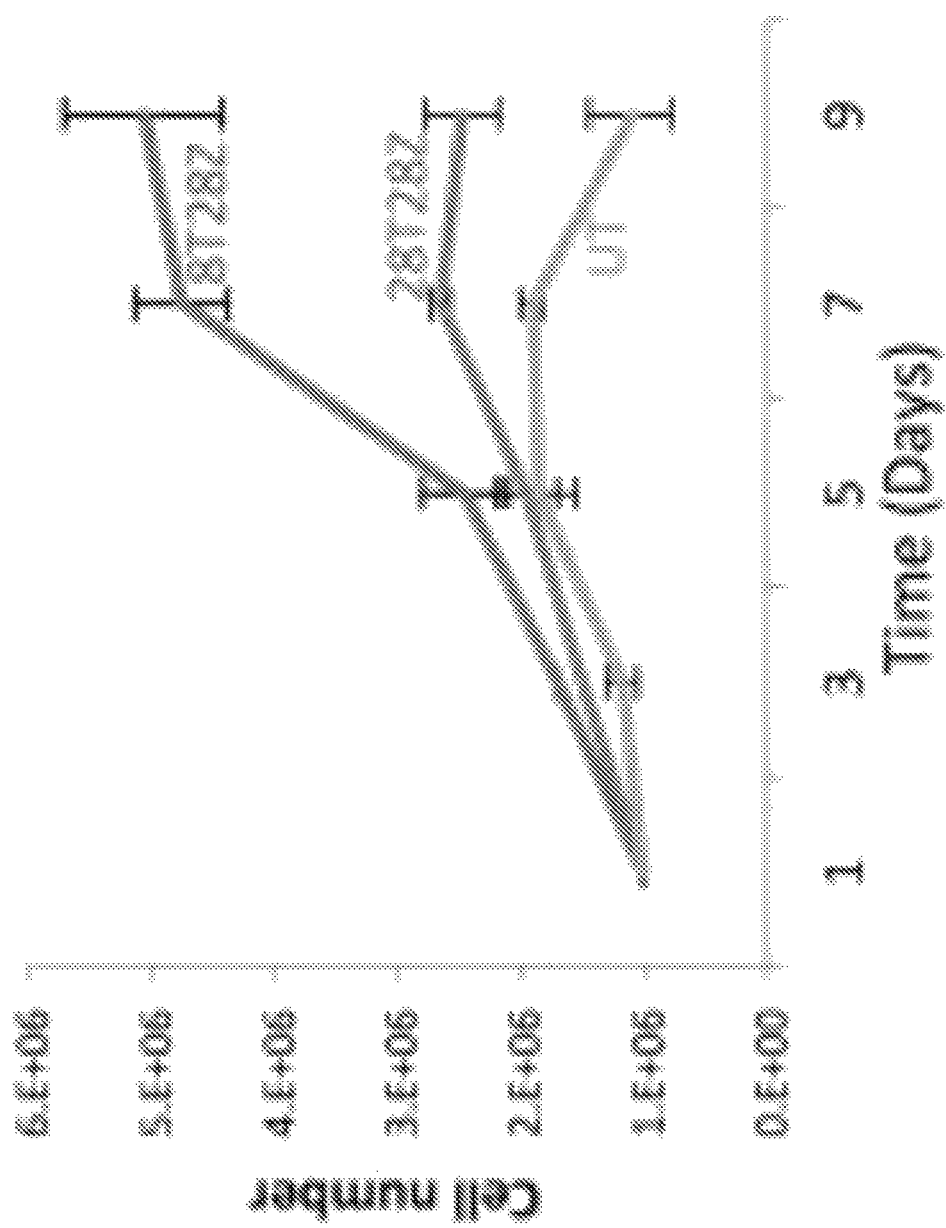

Because most studies so far have been focused on $\alpha\beta$ T cells, new design guidelines tailored to the $\gamma\delta$ subset are necessitated to achieve their full potential. Transduction of $\alpha\beta$ T-cells with either a 8T28Z, a 28T28Z, or a 8TBBZ CAR yielded comparable levels of CAR expression, as measured by Protein-L staining followed by flow cytometry. In contrast, when $\gamma\delta$ T cells from the same donor were transduced with the abovementioned CARs, the 28T28Z CAR displayed substantially lower levels of expression by comparison (FIG. 3B). This result highlights the need for a detailed optimization of each component of the CAR, including those that do not have the ability to transduce signals on their own. The choice of hinge/transmembrane domain had additional consequences in $\gamma\delta$ T-cells: when both CD28-based CARs were compared in their ability to modulate the expression of IL2RB, 8T28Z induced a superior induction of IL2RB membrane expression than 28T28Z, and also a sharp increase in CD27 membrane expression (FIG. 3C). Considering the central role of CD27 in $\gamma\delta$ T-cell biology, this feature of 8T28Z CARs may help increase the efficacy of the resulting CAR-T cells. An increase in sensitivity to IL-2 might be the underlying mechanism whereby 8T28Z-expressing $\gamma\delta$ T-cells display superior ex vivo expansion than 28T28Z counterparts and/or untransduced T cells (FIG. 3D).

Next, a clonotypic analysis was conducted based on TCR Gamma-chain VDJ recombination quantification, to test whether genetic manipulation and/or expression of a CAR resulted in clonal selection of a dominant population of $\gamma\delta$ T cells. This phenomenon has been reported in $\alpha\beta$ T-cells engineered to express growth factors, such as IL15, and since certain CARs favor the growth of transduced $\gamma\delta$ T-cell populations, their heterogeneity was assessed, demonstrating that the overall richness of the culture decreased over time, in all groups (untransduced or CAR-expressing). This means that certain T-cell clones were lost during the process of ex vivo expansion and genetic modification. Importantly however, the overall clonal distribution remained unchanged through the process, and across experimental groups.

Figure 4A:
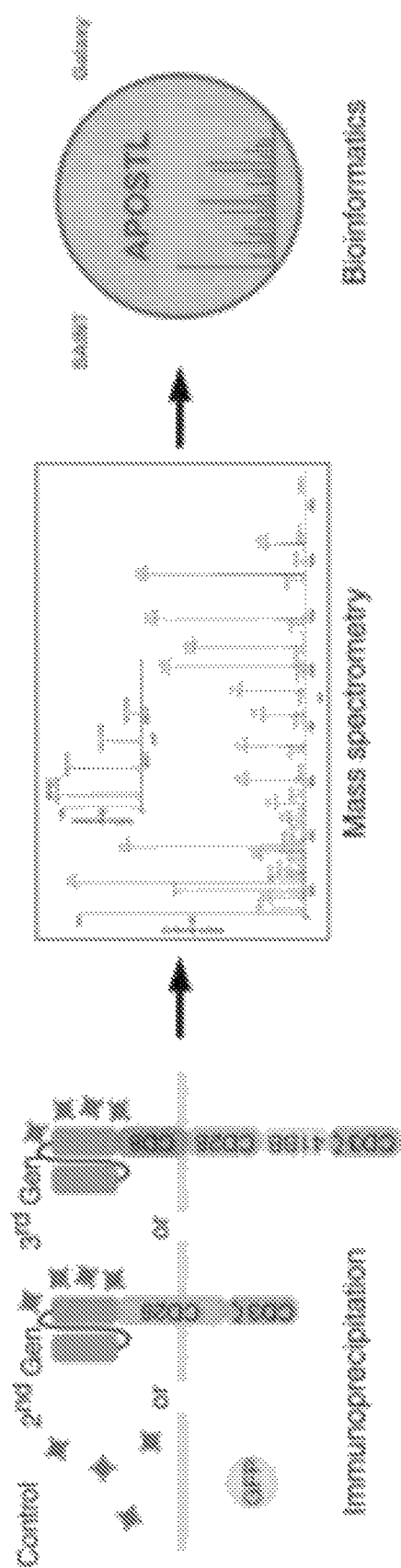
FIGS. 4A to 4D shows immunoproteomic approach.
Figure 4B:
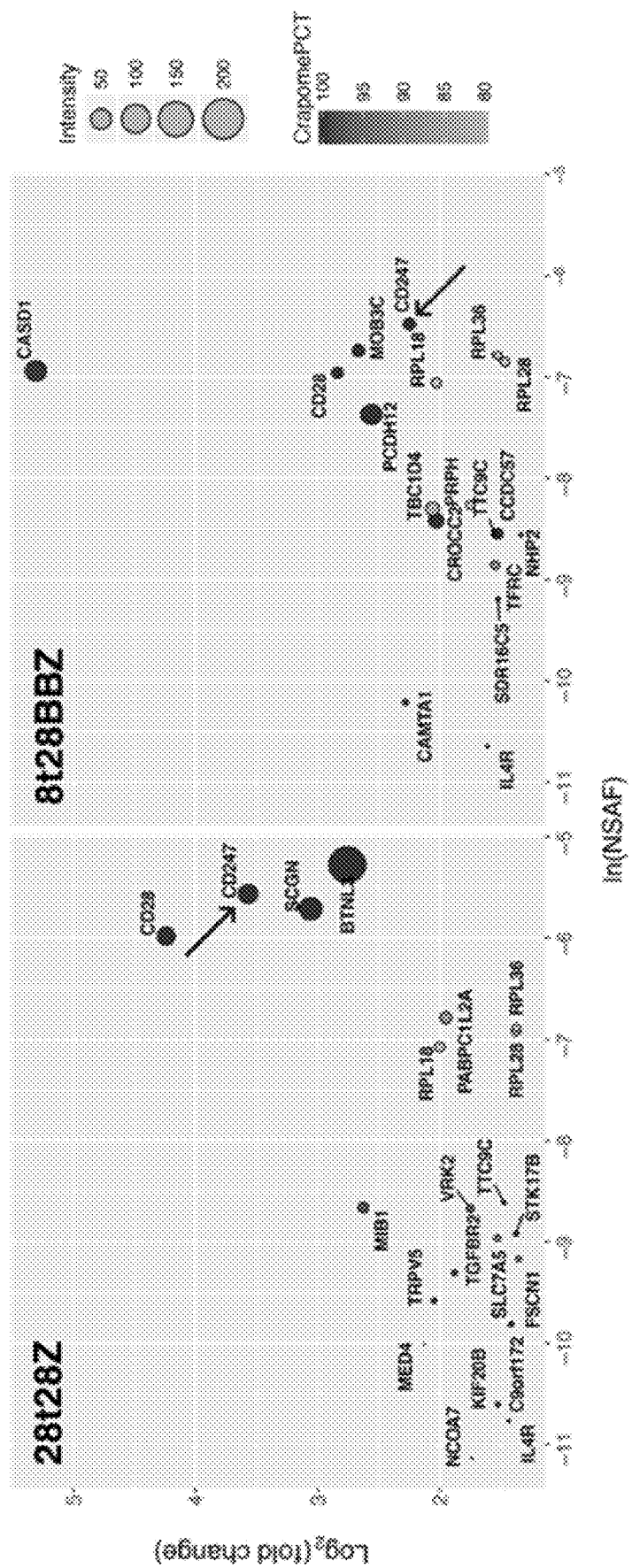
Figure 4C:
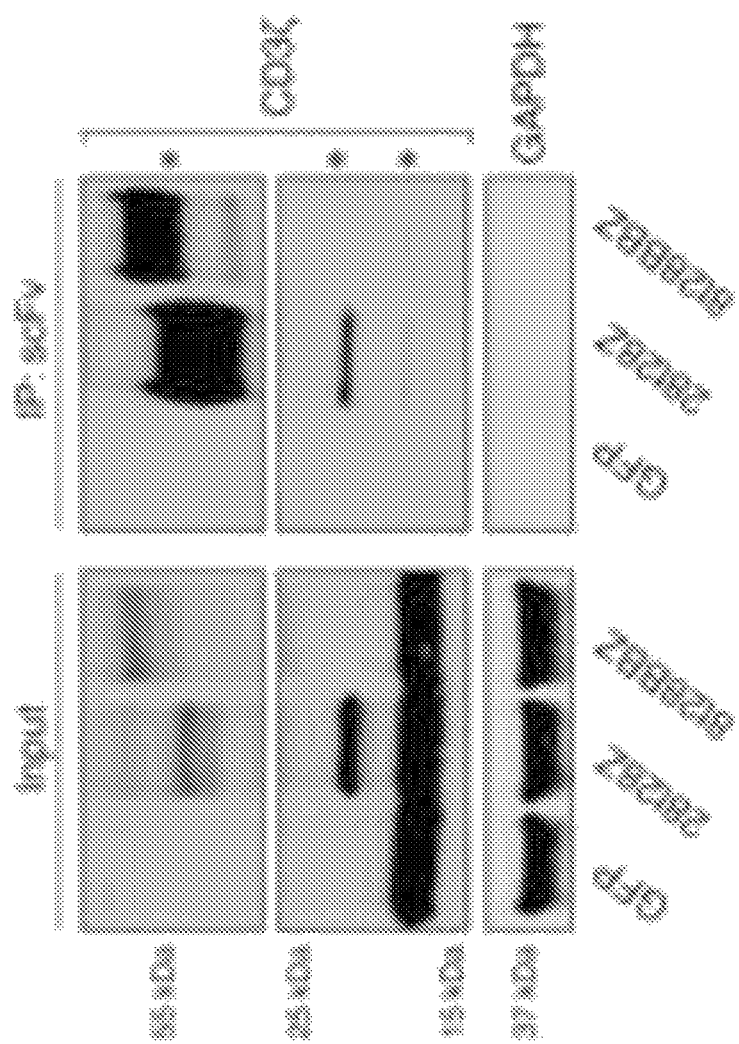
Figure 4D:
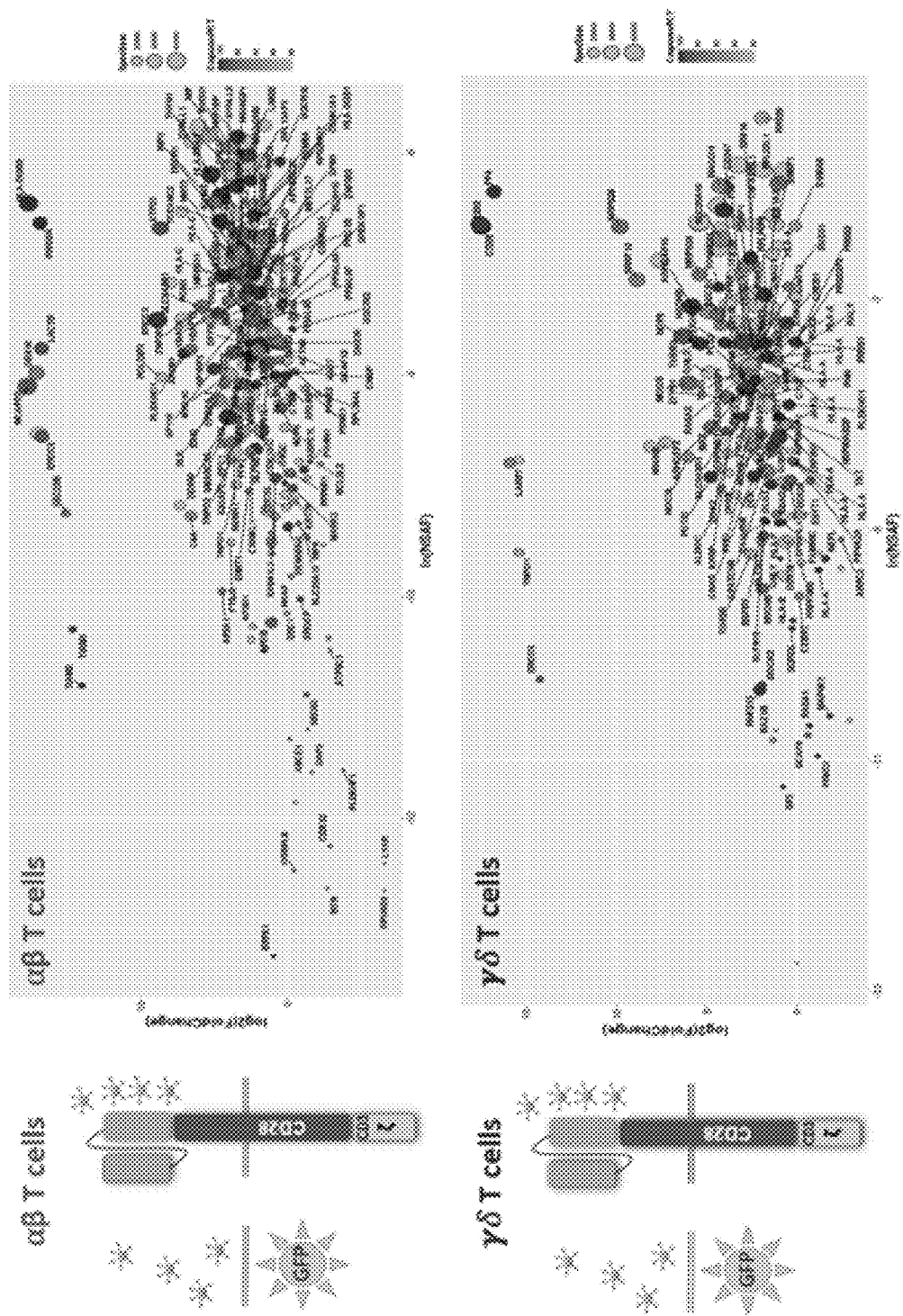

New strategies were explored for the rational design of enhanced CARs, including the development of a mass spectrometry-based method to characterize the signaling and/or adaptor proteins that bind to the CAR molecule. To that end, the CARs were immunoprecipitated using protein-L magnetic beads, which bind the CAR ectodomain, and identified the CAR-bound proteins using tandem liquid chromatography (LC)-mass spectrometry (MS)/MS. CAR interaction partners were shortlisted based on differential abundance between the immunoprecipitates of CAR-transduced T-cells and background controls (GFP-transduced T cells), plus topological properties, using the APOSTL software (ref Kuenzi) (FIG. 4A). When the interactomes of 2 variations of an anti-PSCA CAR (FIG. 4B) in $\alpha\beta$ T-cells we compared, only the 28T28Z CAR was able to interact with, and induce phosphorylation of, a lower molecular weight species of CD3 (FIG. 4C). This trait correlated with superior antitumor efficacy and more potent signaling. The same technology was then applied to characterize the interactome of a single CAR expressed in either $\alpha\beta$ or $\gamma\delta$ T-cells. Using this approach, 37 proteins were identified that were enriched in the CAR immunoprecipitate of $\alpha\beta$ T-cells, and 38 proteins enriched in the CAR immunoprecipitate of 0 T cells (FC CAR/GFP>2, p<0.05, proteins identified by >2 peptides). Among these, certain proteins were only significantly enriched in one of the cell types. For instance, T Cell Lymphoma Invasion And Metastasis 1 (TIAM1) coimmunoprecipitates with the 28T28Z CAR only in $\alpha\beta$ T cells. On the other hand, STK10, a kinase that has been reported to inhibit TCR signaling, was significantly enriched in the CAR immunoprecipitates of 0 but not $\alpha\beta$ T-cells.

Figure 5:
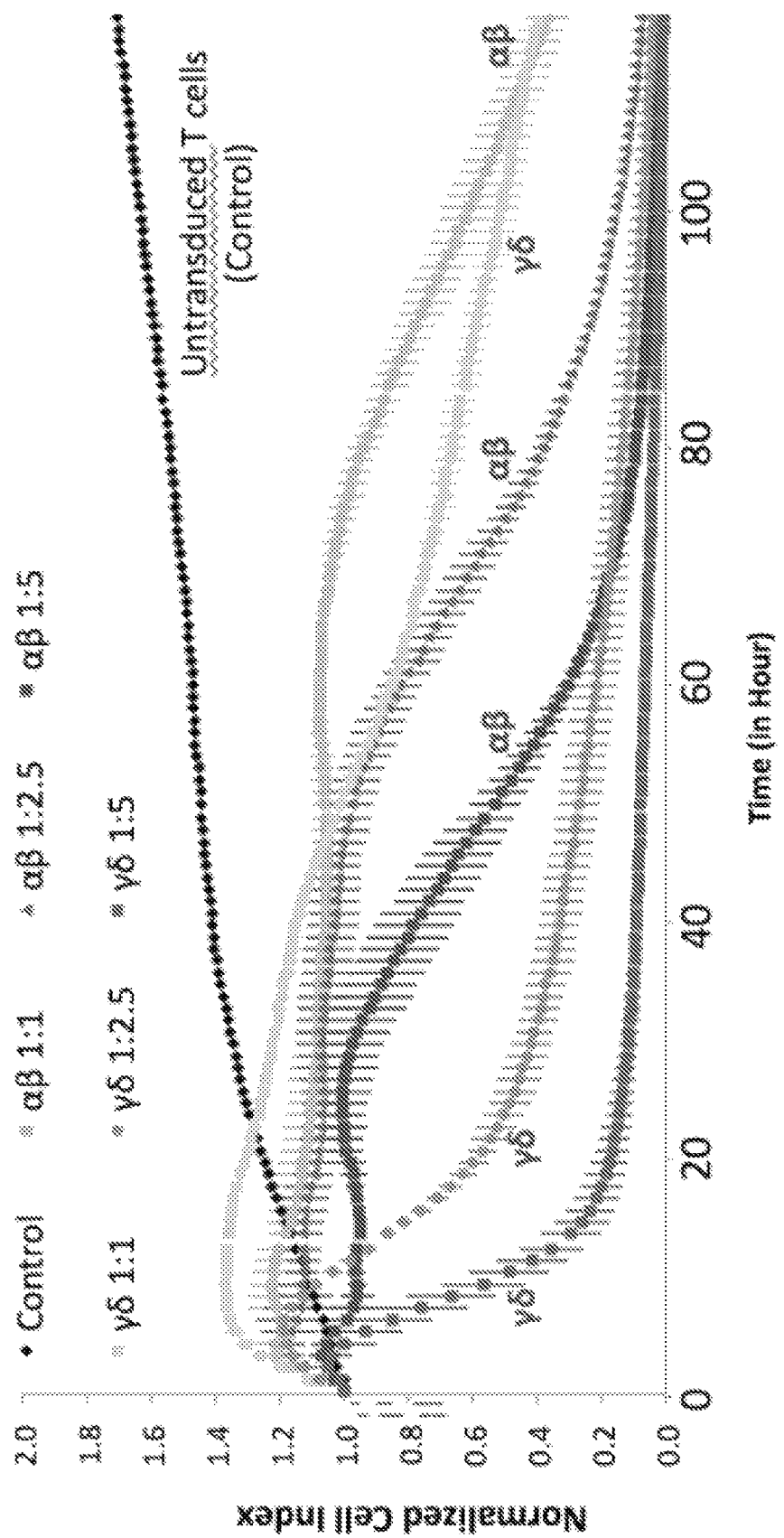
FIG. 5 shows cytotoxicity of 4 vs. γδ CAR-T cells. RTCA analysis of HPAC cells, co-cultured with anti-PSCA CAR-T cells, derived from 4 or γδ T-cells from the same donor. Each curve represents a different Target:Effector ratio (1:5, 1:2.5, 1:1).

The anti-tumor efficacy of PSCA-targeted CARs has been documented in a pre-clinical animal model. Intravenous administration of 28T28Z CAR-T cells resulted in eradication of established cancers. The same cell line was used to test the in vitro cytolytic activity of $\gamma\delta$ CAR-T cells, in comparison with $\alpha\beta$ CAR-T cells generated from the same donor. The cytotoxic efficacy of CAR-T cells was assessed using the ACEA's xCELLigence real-time cytotoxicity assay (RTCA) assay, and 3 different target:effector ratios were used, namely, 1:1, 1:2.5, and 1:5. In each of the 3 conditions, $\gamma\delta$ CAR-T cells induced a faster decrease in cancer cell viability, suggesting that they are more potent and/or faster cytotoxic effectors than $\alpha\beta$ CAR-T cells (FIG. 5). Therefore, in addition to controlled trafficking and TCR-based recognition of zol-treated cells, 0 CAR-T cells present an additional advantage over $\alpha\beta$ counterpart based on their intrinsically higher cytolytic potential.

Figures 6A, 6B:
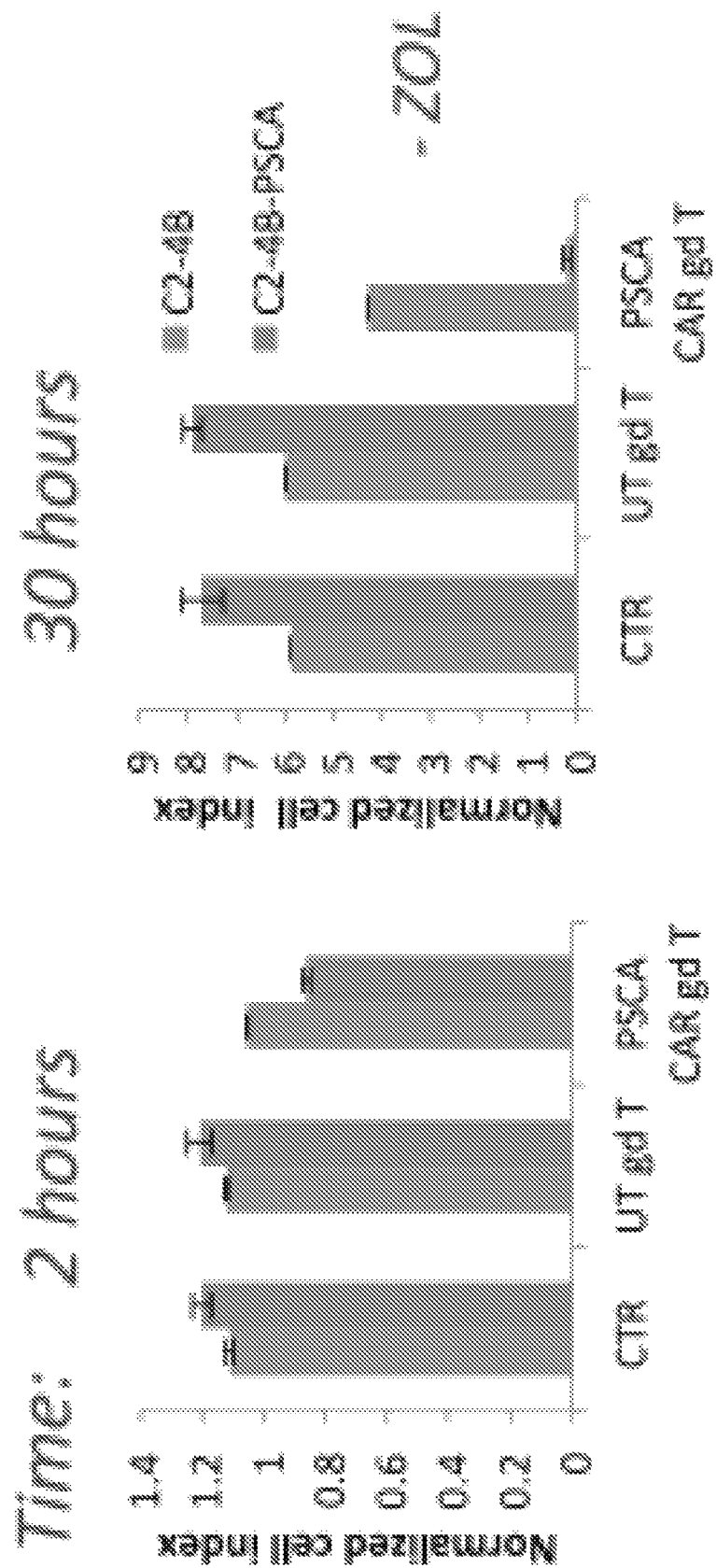
FIGS. 6A to 6D show zoledronate increases γδ T-cell cytotoxic activity against C4-2B. Summary of RTCA analysis of C4-2B-PSCA, or control PSCA null C4-2B, cells co-cultured with γδ CAR-T cells, or untransduced controls (UT).
Figures 6C, 6D:
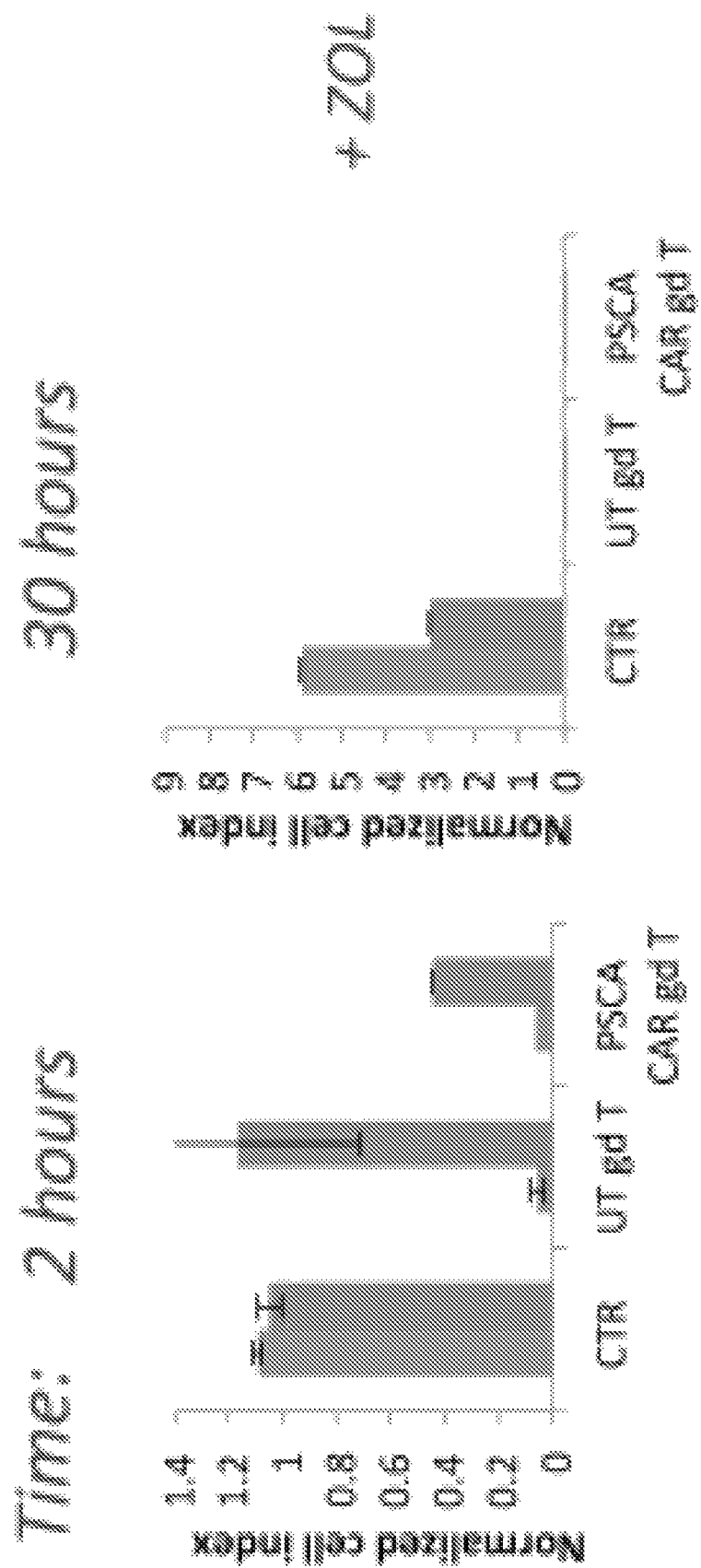

The CAR- and TCR-mediated mechanism of tumor cell recognition were tested using the CRPC C4-2B cell line. Parental C4-2B, or PSCA-overexpressing C4-2B-PSCA cells were treated with untransduced (UT) or CAR-transduced $\gamma\delta$-T-cells, in presence or absence of zoledronate, and the viability of tumor cells was expression, had induced a notable reduction in the viability of C4-2B cells when given in combination with zoledronate. This effect was less evident in C4-2B-PSCA cells, and no cytotoxicity was detected in either group in absence of zoledronate. By 30 hours, γδ CAR-T cells had eliminated virtually 100% of the C4-2B-PSCA culture in absence of zoledronate treatment, with minimal effect on the parental cells. When zoledronate was used in combination with γδ T-cells, γδ T-cells fully eradicated the tumor cells, regardless of PSCA or CAR expression (FIG. 6)

Next, the anti-tumor activity of γδ T-cells on established bone metastatic CRPC lesions in vivo was assessed. NSG (NOD.Cg-Prkdcscid112rgtm1Wjl/SzJ) immunocompromised mice were intratibially inoculated with C4-2B luciferase expressing cells ($1 \times 10^5$) and once established were randomized in zoledronate (0.1 mg/Kg) or vehicle (saline) groups (n=25 per group) based on relative luminescence unit (RLU) measurement. One week later, mice received tail vein injections of human γδ T-cells (3.5×106/mouse).

Figure 7A:
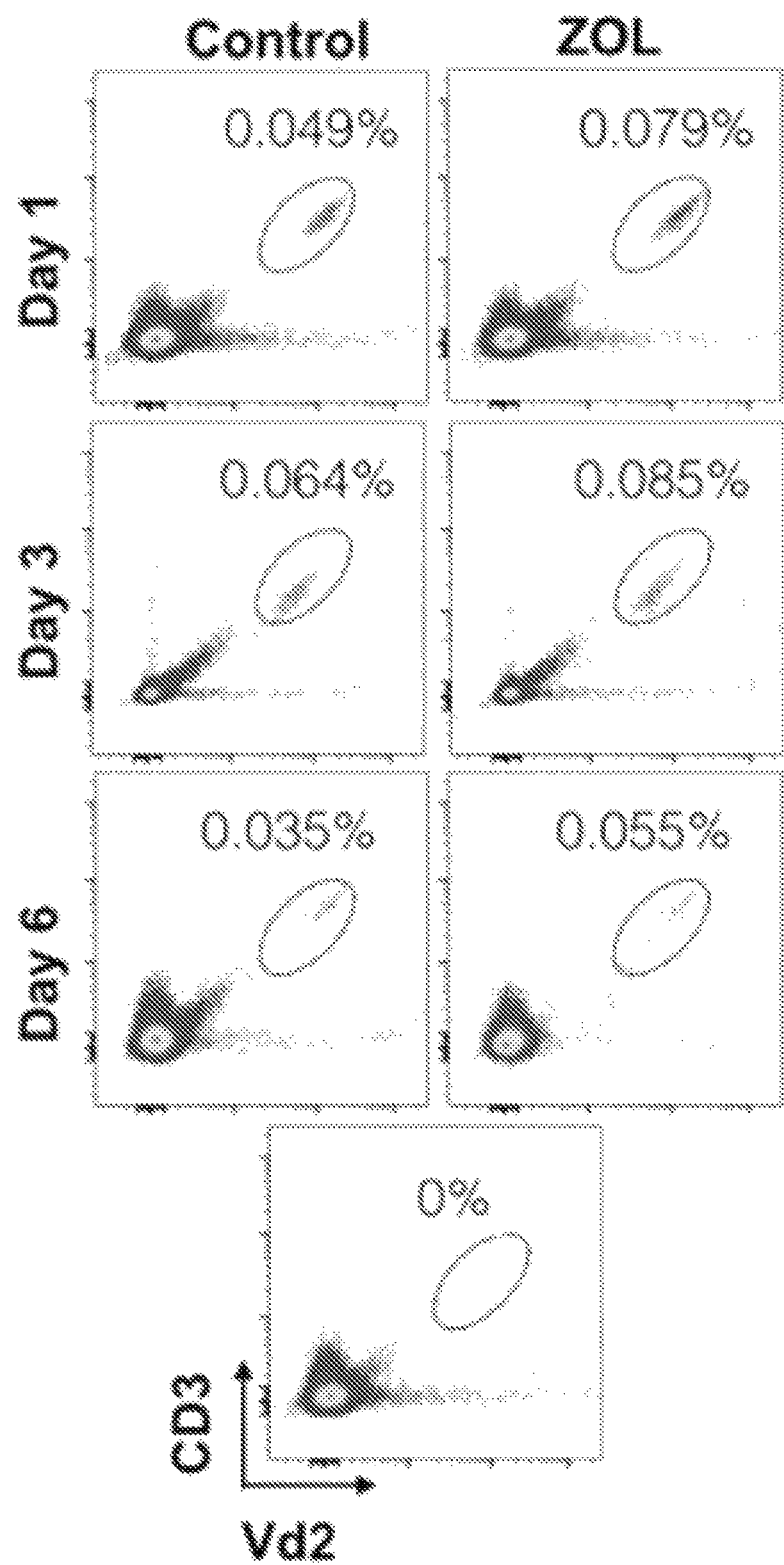
Figures 7B, 7C:
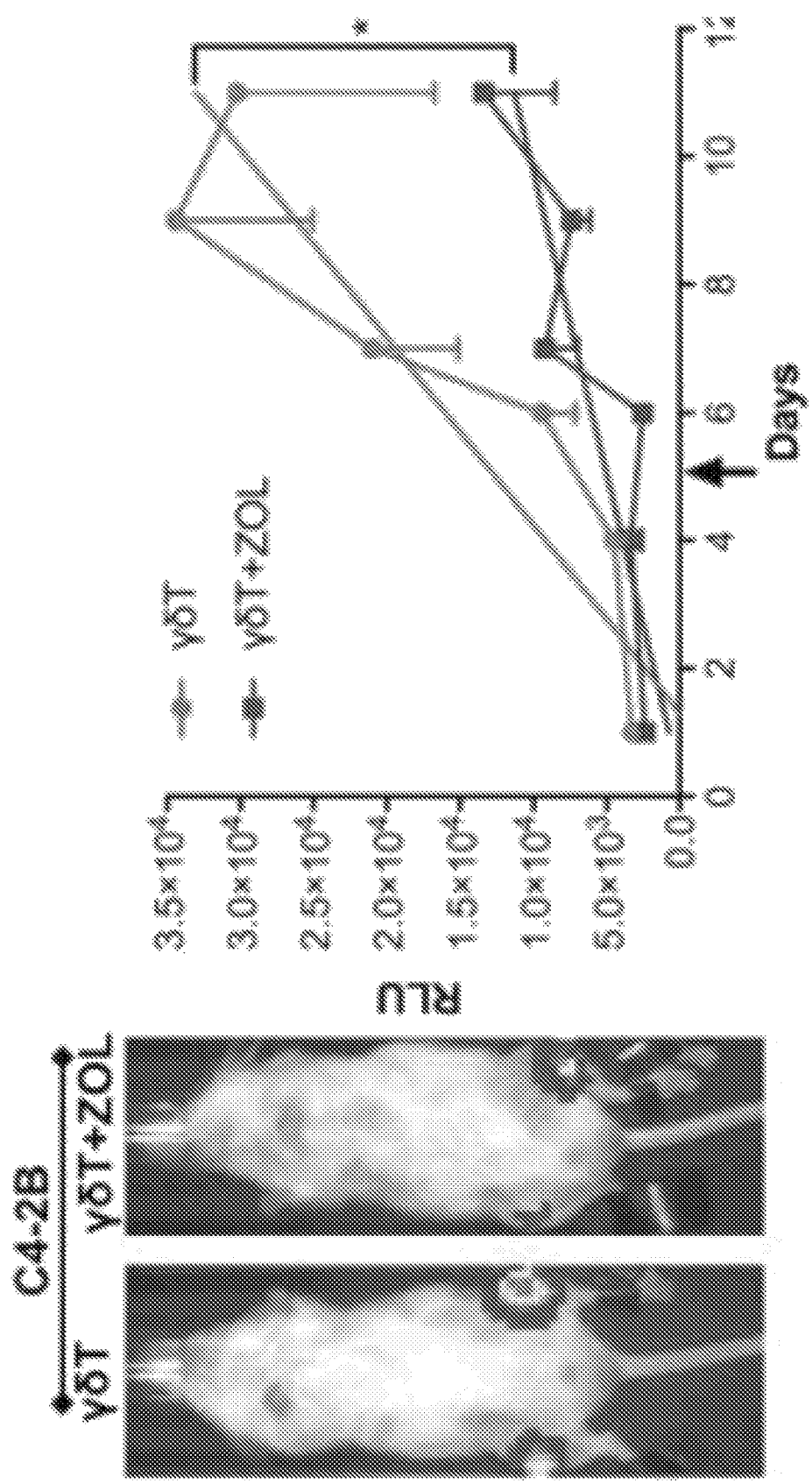
Figure 7D:
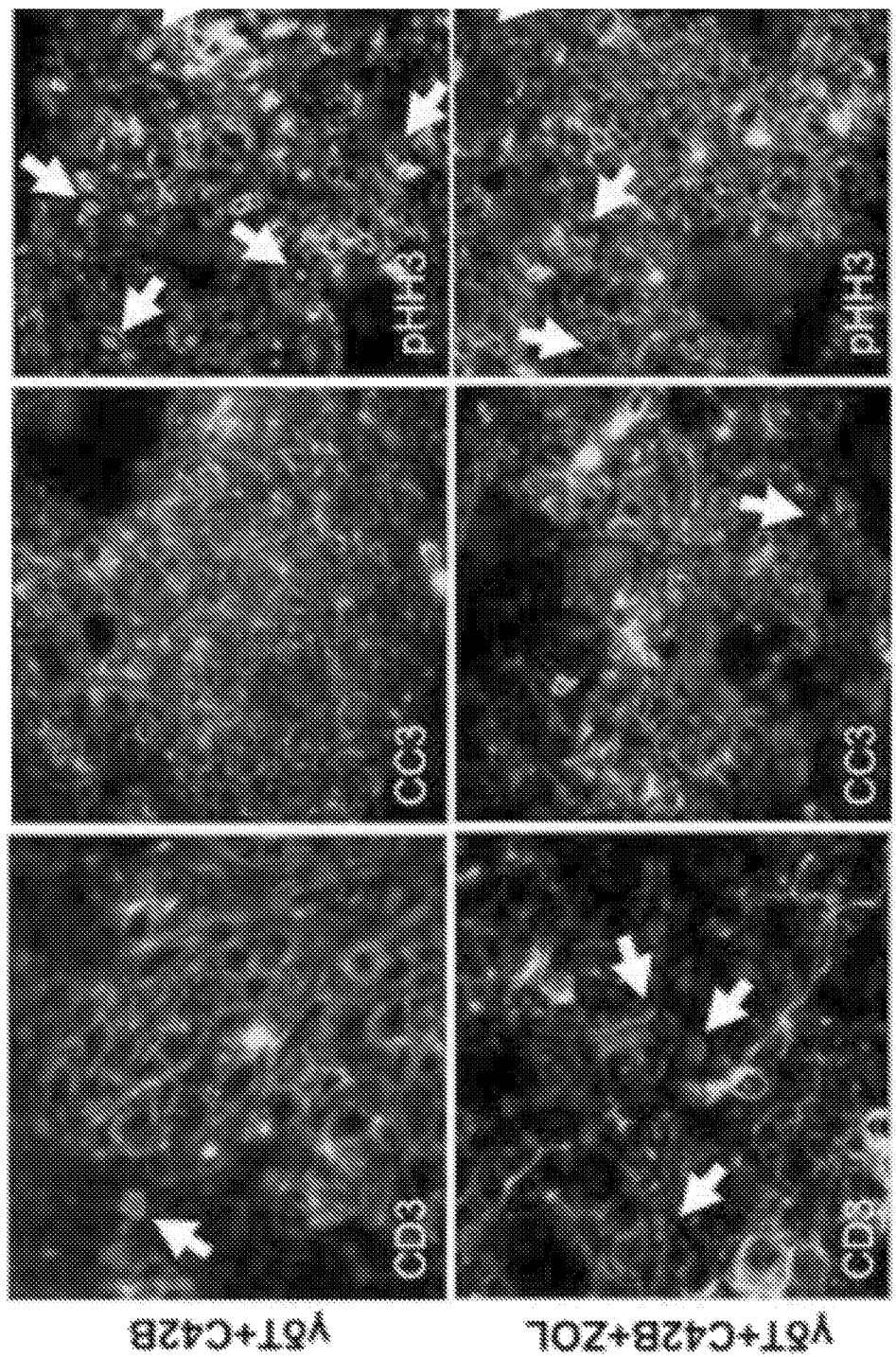

Groups of mice (n=5) were removed from the study 1, 3, 5 days subsequent to injection with tibias being flushed and assessed for human CD3 Vd2 content by flow cytometry. Data show that the percentage of CD3Vd2 positive cells was consistently higher in the zoledronate group compared to control at Day 1 (>61%), 3 (>32%) and 5 (>57%) (FIG. 7A). Bioluminescence was used as a correlate of tumor growth. The C4-2B growth rate was significantly slower in the zoledronate group compared to the controls (FIG. 7B, 7C). Histological analysis of tibias at the study endpoint revealed the presence of human CD3 cells in the tumor bone microenvironment with increased apoptotic (cleaved caspase-3) and decreased proliferative (phospo-Histone H3) cancer cells in the zoledronate group compared to control. The C4-2B cell line model generates bony lesions in vivo and both control and zoledronate treated tumors were heavily infiltrated with MSCs. Analysis of human specimens of bone metastatic prostate cancer (n=10) revealed the presence of CD3 positive T-cells and α-smooth muscle actin (αSMA) positive MSCs throughout the host microenvironment underscoring the presence of this population in these lesions.

CONCLUSIONS

IPP generated from zoledronate promotes γδ T-cell activity. Selection of CAR costimulatory domains is critical for γδ CAR-T cytotoxicity. γδ T-cells have distinct costimulatory binding domains compared to αβ T-cells. γδ CAR-T cells have superior cytotoxic activity to PSCA expressing cancer cells compared to αβ T-cells and that efficacy can be enhanced by zoledronate. In vivo zoledronate enhances the recruitment and cytotoxic effect of γδ CAR-T cells on bone metastatic prostate cancer cells. Conditioned media derived from bone marrow MSCs enhances γδ T-cell activity.

Example 2

Figure 8:
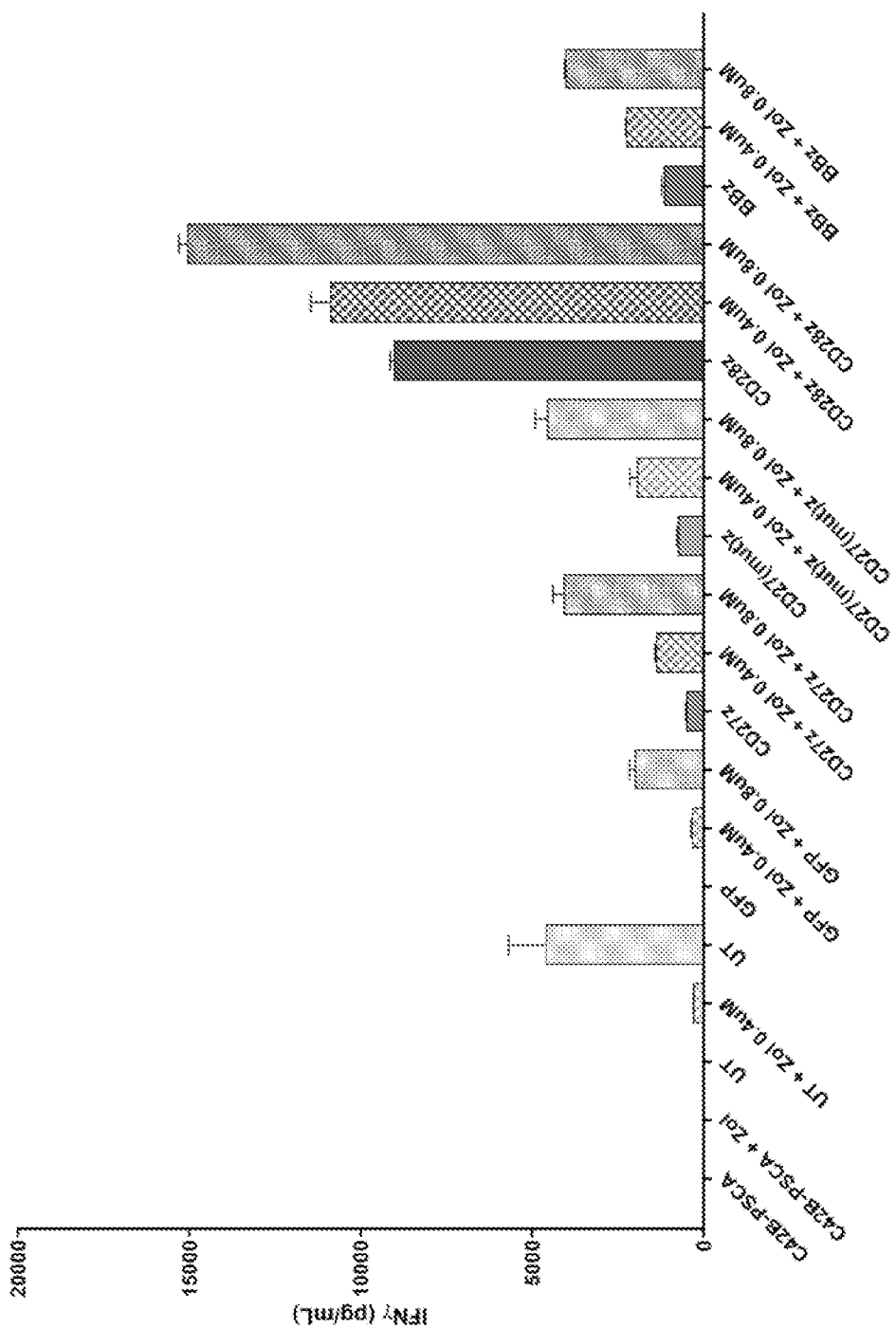
FIG. 8 shows the effects of zoledronate treatment on cytokine production by γδ CAR-T cells containing diverse costimulatory domains, in presence or absence of bisphosphonate treatment.

FIG. 8 shows the effects of zoledronate treatment on cytokine production by γδ CAR-T cells containing diverse costimulatory domains. Four variants of the anti-PSCA CAR were generated containing either CD27 (CD27z), CD28 (CD28z), or 4-1BB (BBz) costimulation. The fourth variant contains a CD27 costimulatory domain where the TRAF-binding site has been replaced with an inert flexible linker (G4S). γδ CAR-T cells expressing either CAR variant (or GFP as controls) were generated, and cocultured with PSCA-expressing C42B prostate cancer cells, in presence or absence of zoledronate, at the indicated doses. The presence of interferon-γ in the supernatants (measured by ELISA) was used as a marker of T cell activation. CAR-expressing T cells (but not untransduced or GFP-transduced cells) reacted to target cells by producing interferon-γ (solid bars). Addition of zoledronate induced target recognition by GFP-transduced and untransduced γδ T cells, and enhanced interferon production by CAR-T cells, indicating that the recognition of phosphoantigens by the endogenous γδ TCR remains functional in all cells. The highest levels of cytokine secretion were observed for the CD28-containing CAR-T cells.

Figure 9A:
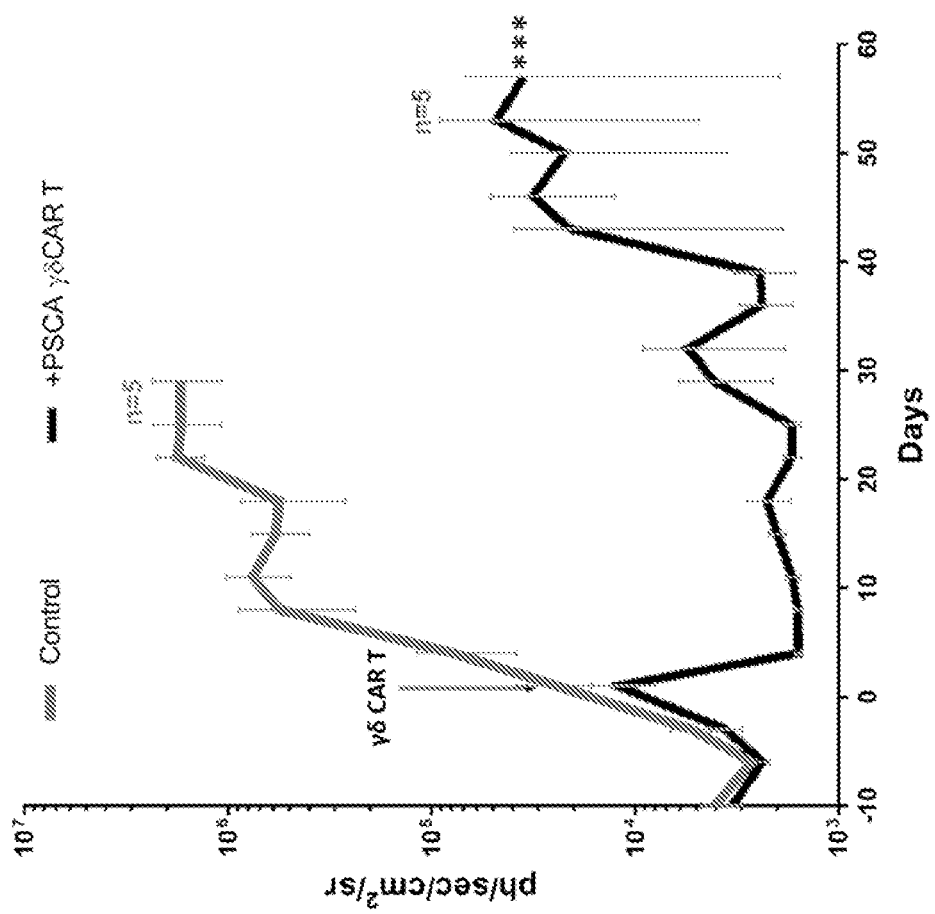
FIGS. 9A and 9B show the effect of anti-PSCA γδ CAR-T cells in vivo on tumor growth (FIG. 9A) and overall survival (FIG. 9B).
Figure 9B:
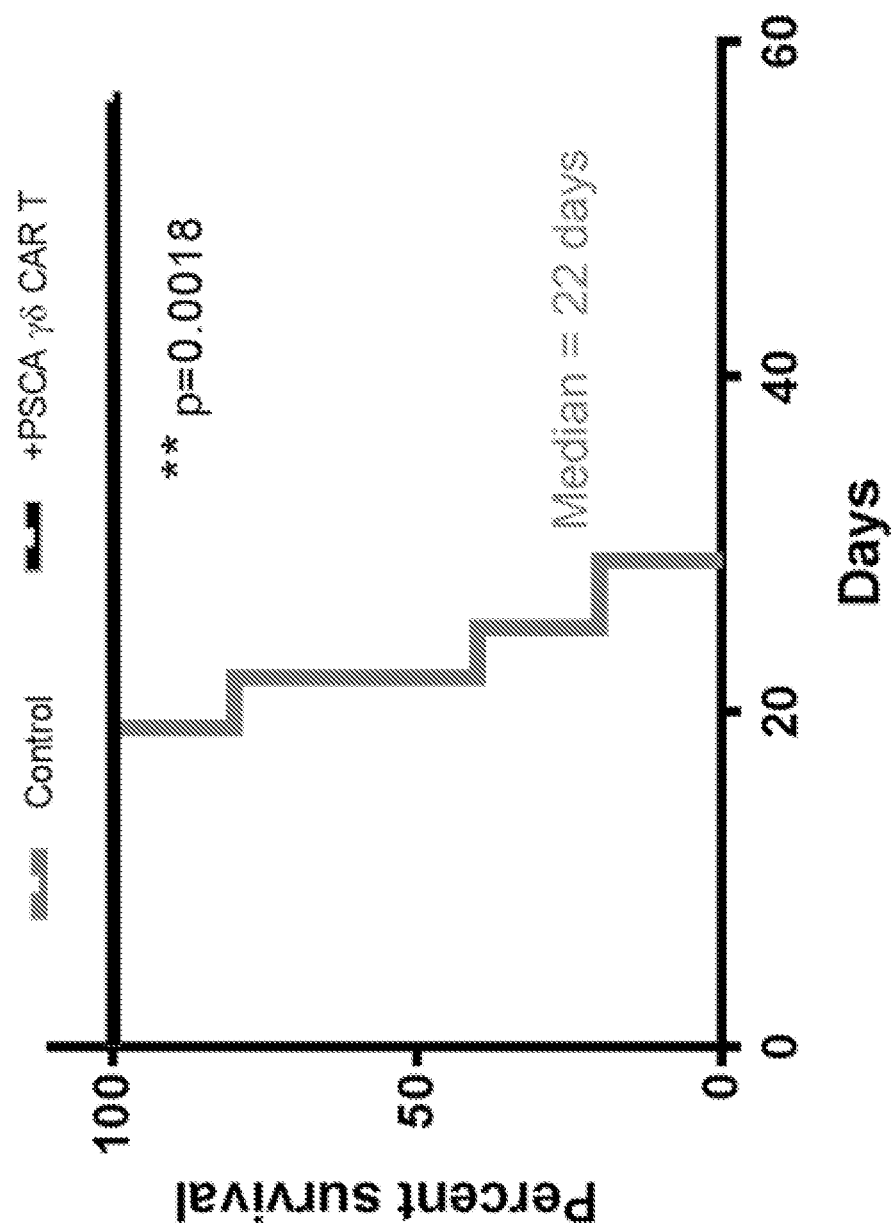

FIGS. 9A and 9B show the effect of anti-PSCA γδ CAR-T cells in vivo on tumor growth (FIG. 9A) and overall survival (FIG. 9B). To test the effect of anti-PSCA γδ CAR-T cells in vivo, male NSG mice were intratibially injected with PSCA- and Luciferase-expressing C4-2B prostate cancer cells, and treated with a single intravenous dose of γδ CAR-T cells, at day 0. Bioluminescence was monitored over time as a measure of tumor growth (FIG. 9A). CAR-T cell treated mice experienced a rapid and significant (p<0.001) decrease in tumor burden, and a significant (p=0.0018) increase in overall survival, compared to control mice (FIG. 9B).

Figure 10A:
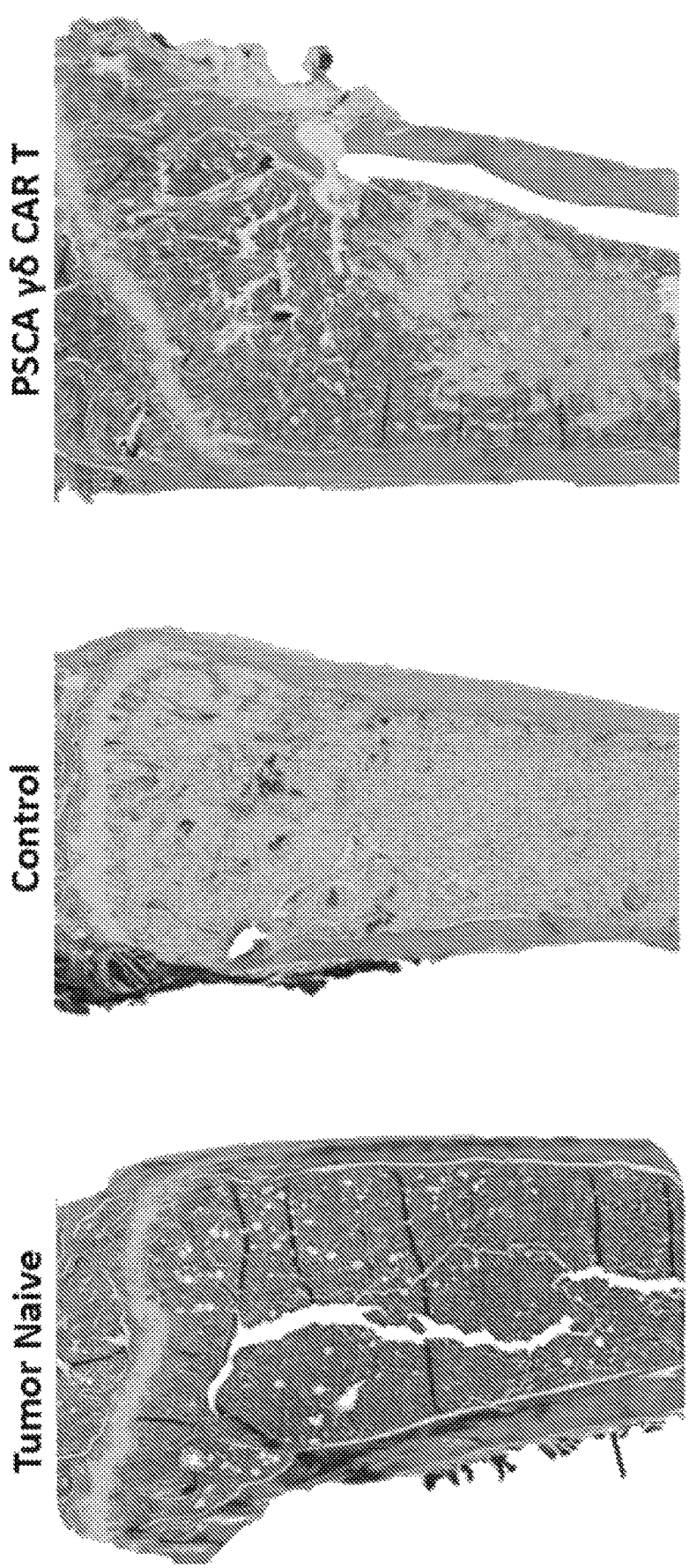
FIGS. 10A to 10D show protection against tumor-induced bone disease.
Figure 10B:
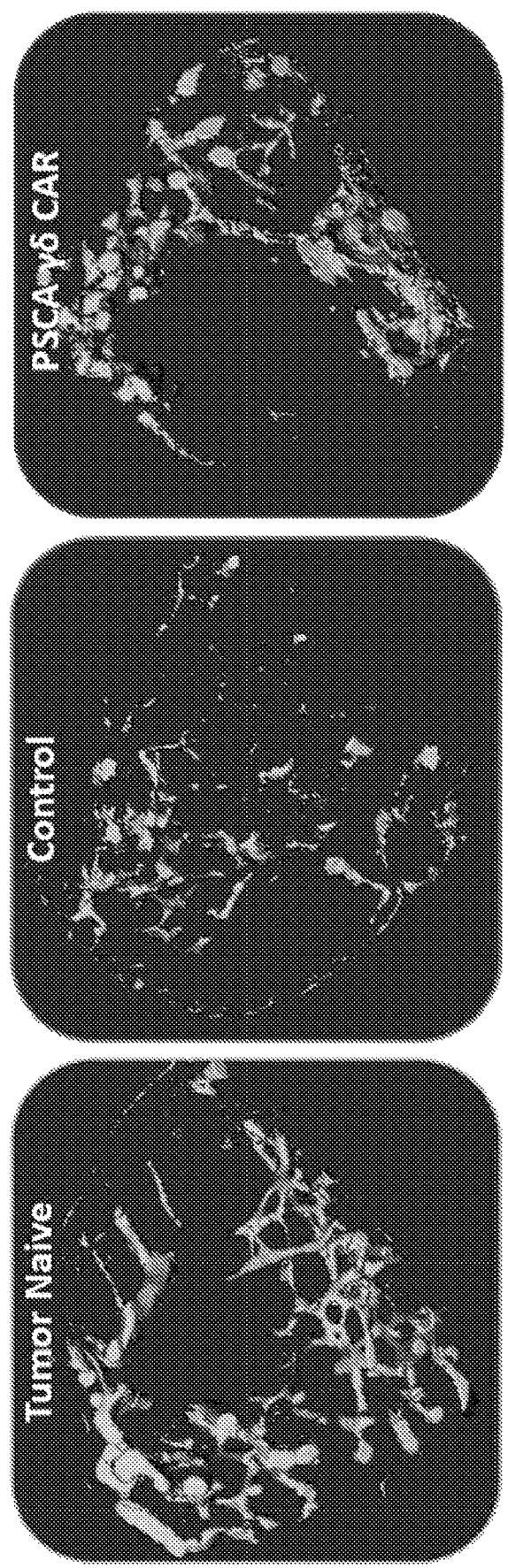
Figure 10C:
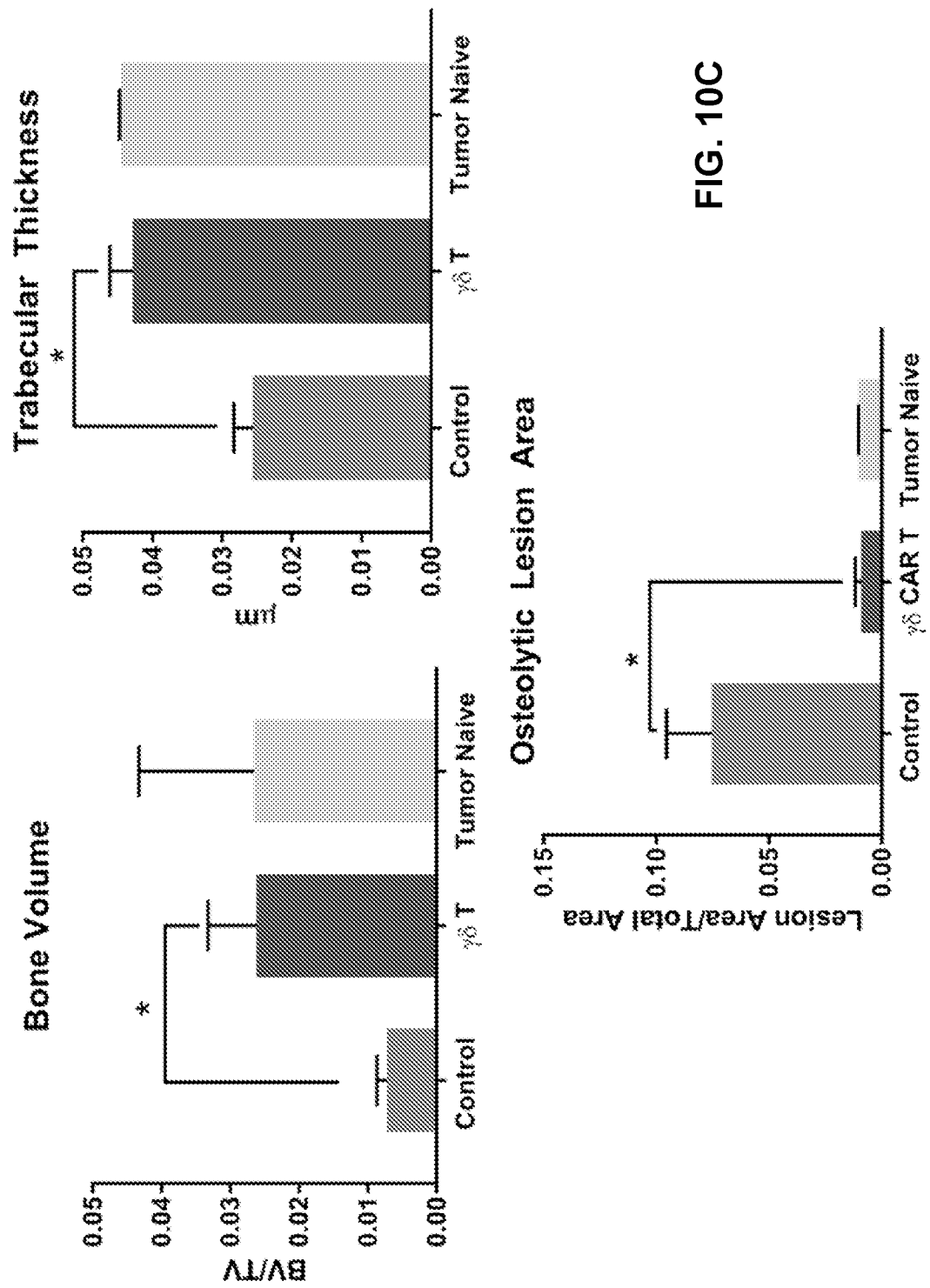
Figure 10D:
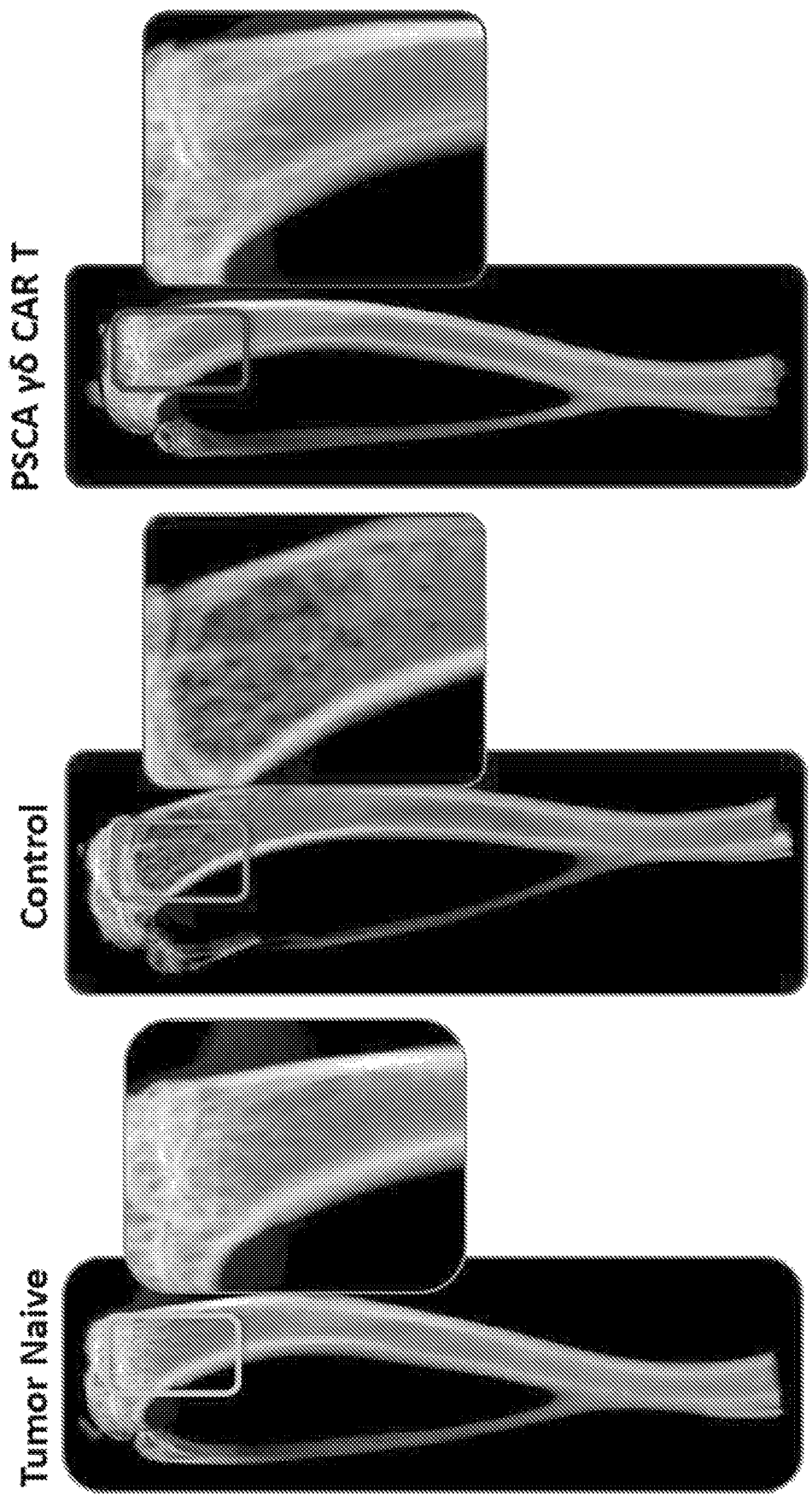

FIGS. 10A to 10D show protection against tumor-induced bone disease. FIG. 12A shows trichrome and hematoxylin histological analysis showing bone and tumor areas in tibia tissue sections. FIG. 10B shows 3D reconstructions of trabecular bone volume from high resolution µCT scanning. FIG. 10C shows quantification of µCT-based analysis of bone architecture. Significantly greater bone volume and trabecular thickness was observed in tibias from animals treated with γδ CAR-T cells. FIG. 10D shows faxitron X-ray analysis showing significant mitigation of cancer-induced osteolysis in animals treated with γδ CAR-T cells.

Figure 11A:
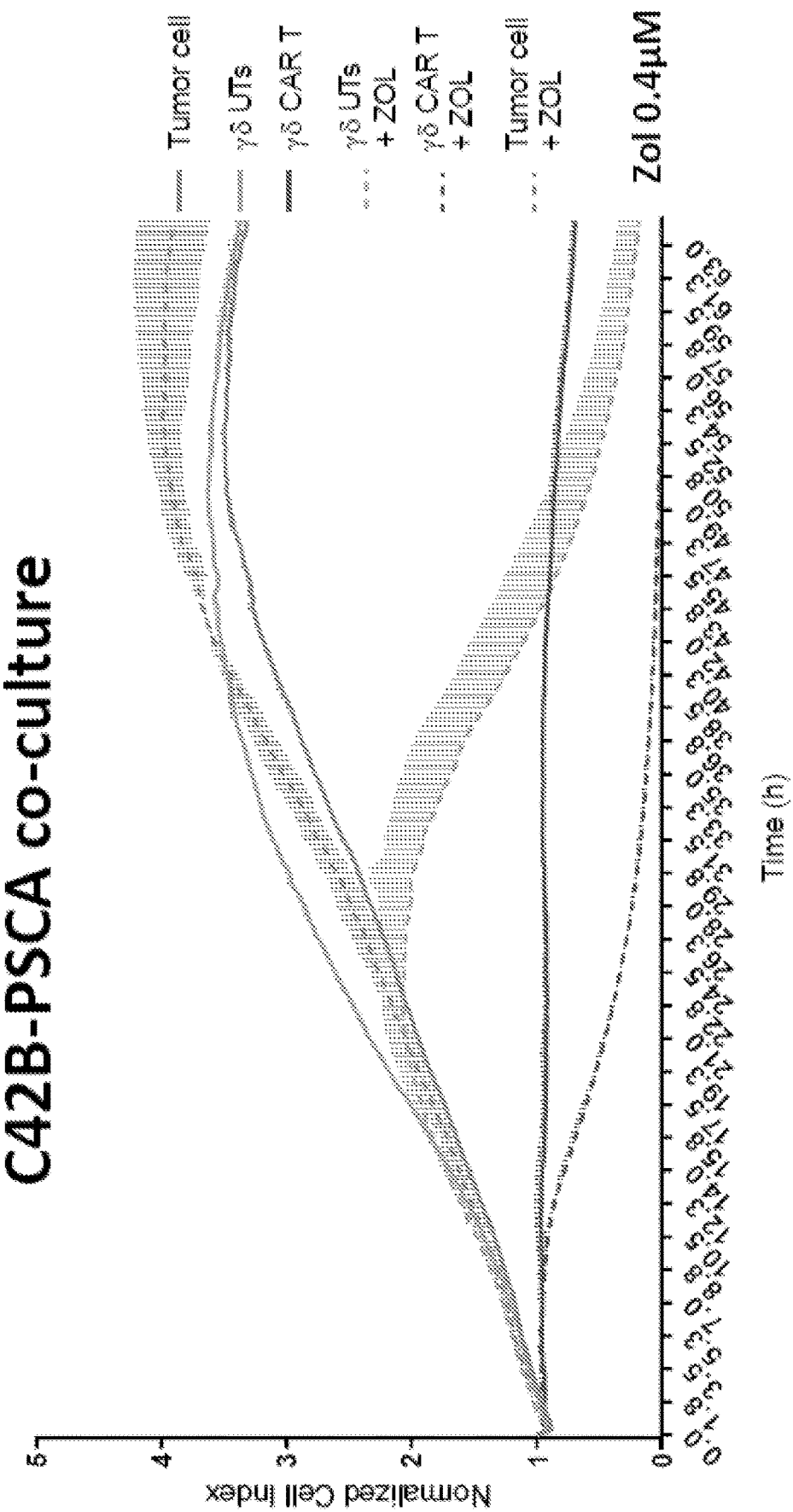
FIGS. 11A and 11B show zoledronate enhances γδ (CAR)-T cells cytotoxic effect.
Figure 11B:
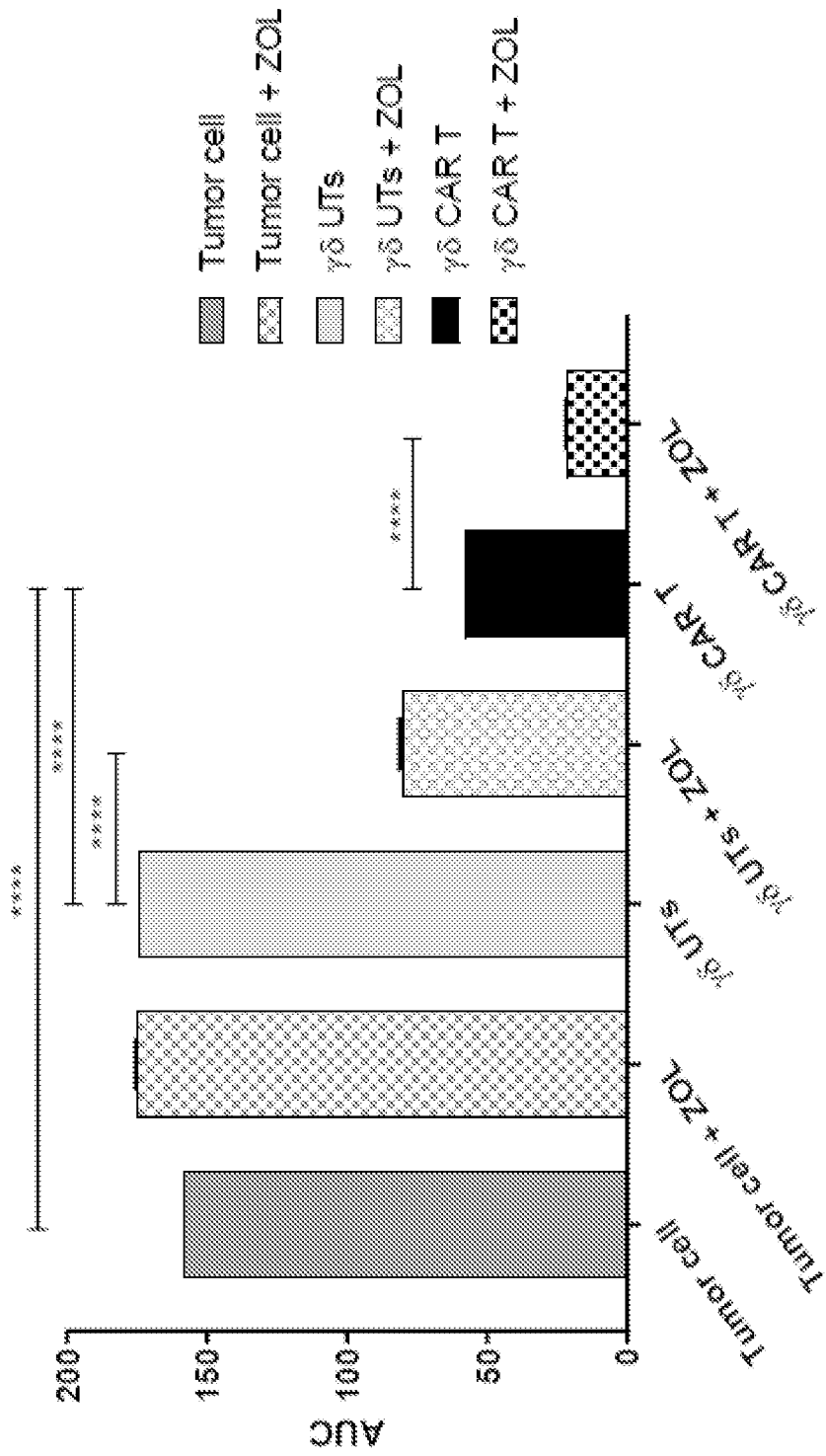
Figure 12:
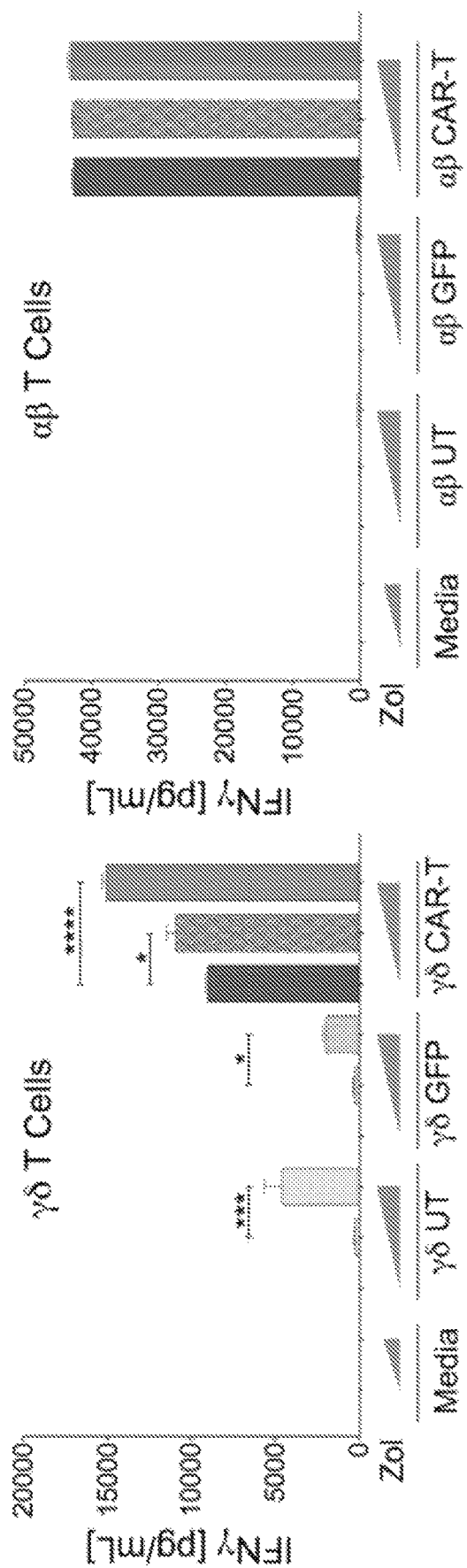
FIG. 12 shows Zol modulates cytokine production only in γδ T cells. IFNγ ELISA of co-culture supernatants of C4-2B-PSCA cells exposed to media (negative control) or the indicated T cells, in presence of increasing concentrations of Zol (0, 0.4 and 0.8 μM).

Example 3

γδ CAR-T cells recognize tumor cells via CAR and via TCR. The CAR- and TCR-mediated mechanisms of tumor cell recognition were tested using the CRPC C4-2BPSCA cell line. Cancer cells were treated with either untransduced (UT) control or CAR-expressing γδ T-cells, in the presence or absence of ZOL (0.4 µM). In presence of ZOL, control γδ T cells induced a cytotoxic effect at approx. 18 h, reflecting recognition of C4-2B-PSCA cells via TCR. Conversely, γδ CAR-T cells induced cytotoxicity from experiment initiation in the absence of ZOL demonstrating the activity of the CAR. Addition of ZOL to the γδ CAR-T greatly enhanced their cytolytic activity resulting in complete elimination of tumor cells by 45 hours (FIG. 11A). Differences in the cumulative cytotoxic effect were statistically significant among groups (FIG. 11B). Moreover, addition of ZOL to a coculture of γδ (CAR−)T-cells with C4-2BPSCA cells enhanced IFNγ secretion. This effect was not observed when αβ were used, which secreted very high levels of IFNγ regardless of ZOL addition (FIG. 12). The ability to induce a potent cytolytic effect with lesser cytokine production that can be modulated by ZOL is important since it may allow γδ (CAR−)T-cells to mediate more precise tumor killing, reducing the risk for complications related to massive cytokine release.

Figure 13:
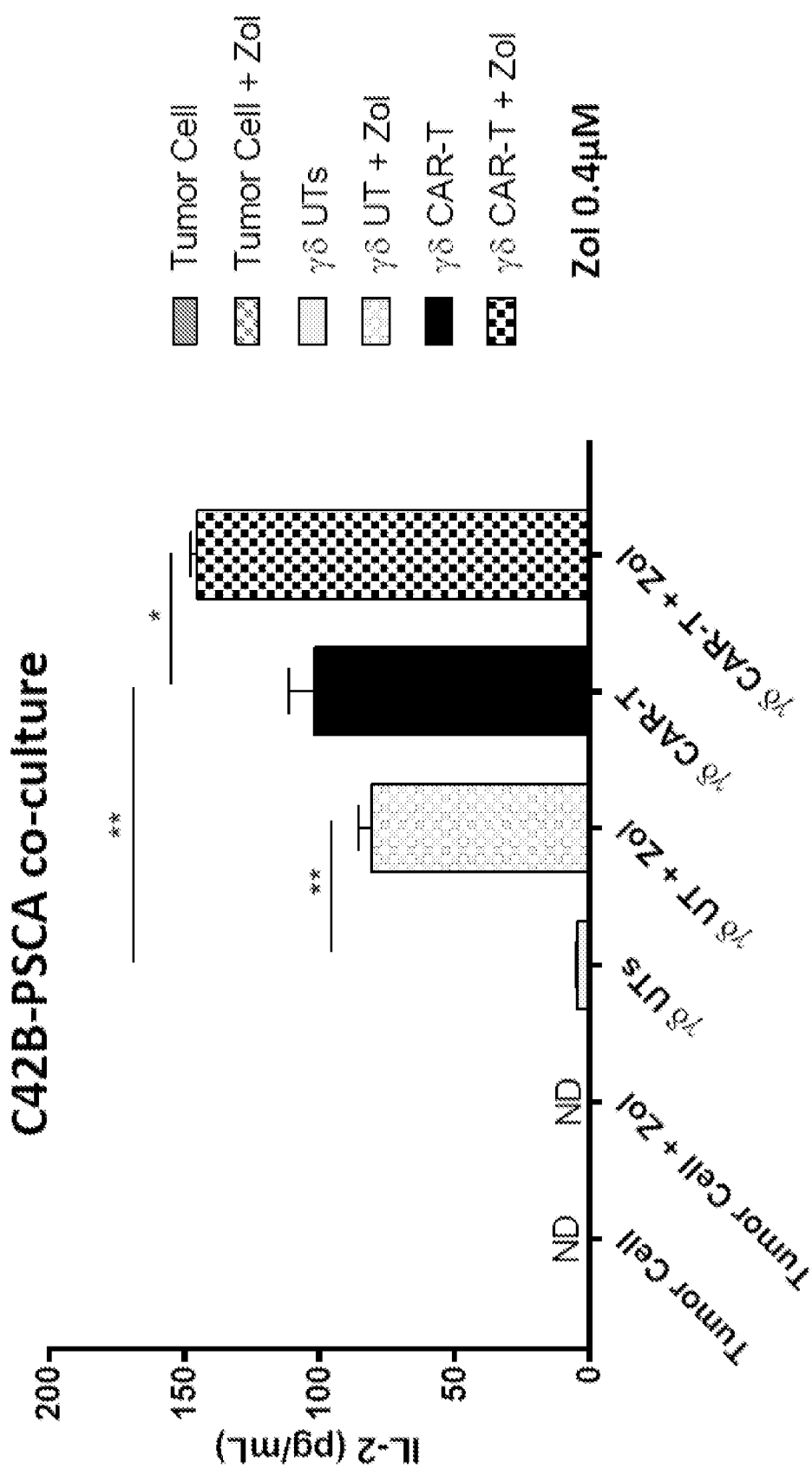
FIG. 13 shows zoledronate increases IL-2 secretion by γδ (CAR)-T cells.

FIG. 13 shows zoledronate increases IL-2 secretion by γδ (CAR)-T cells.

Example 4

Figure 14A:
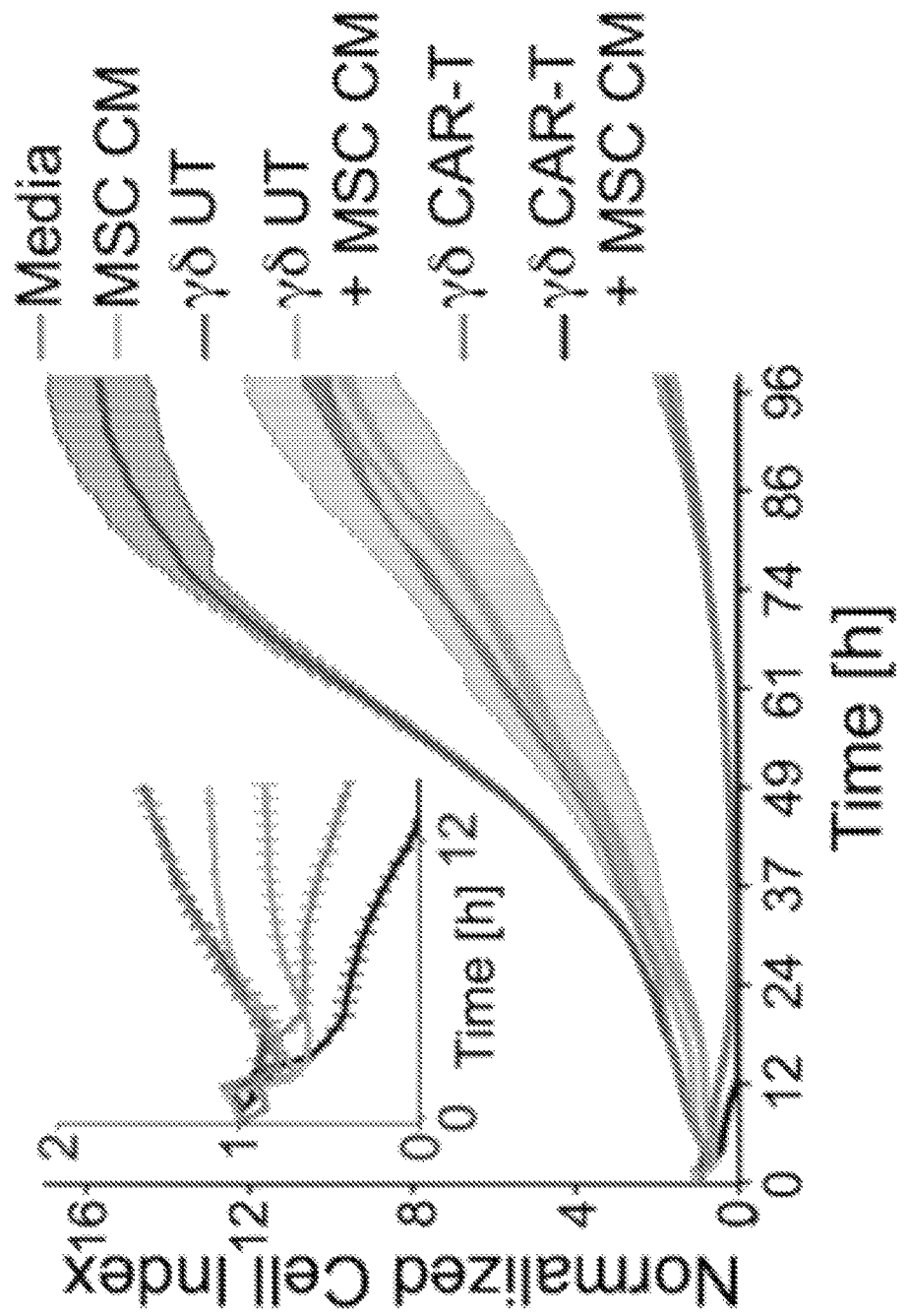
FIGS. 14A and 14B show MSC conditioned media (CM) increases T-cell cytotoxicity.
Figure 14B:
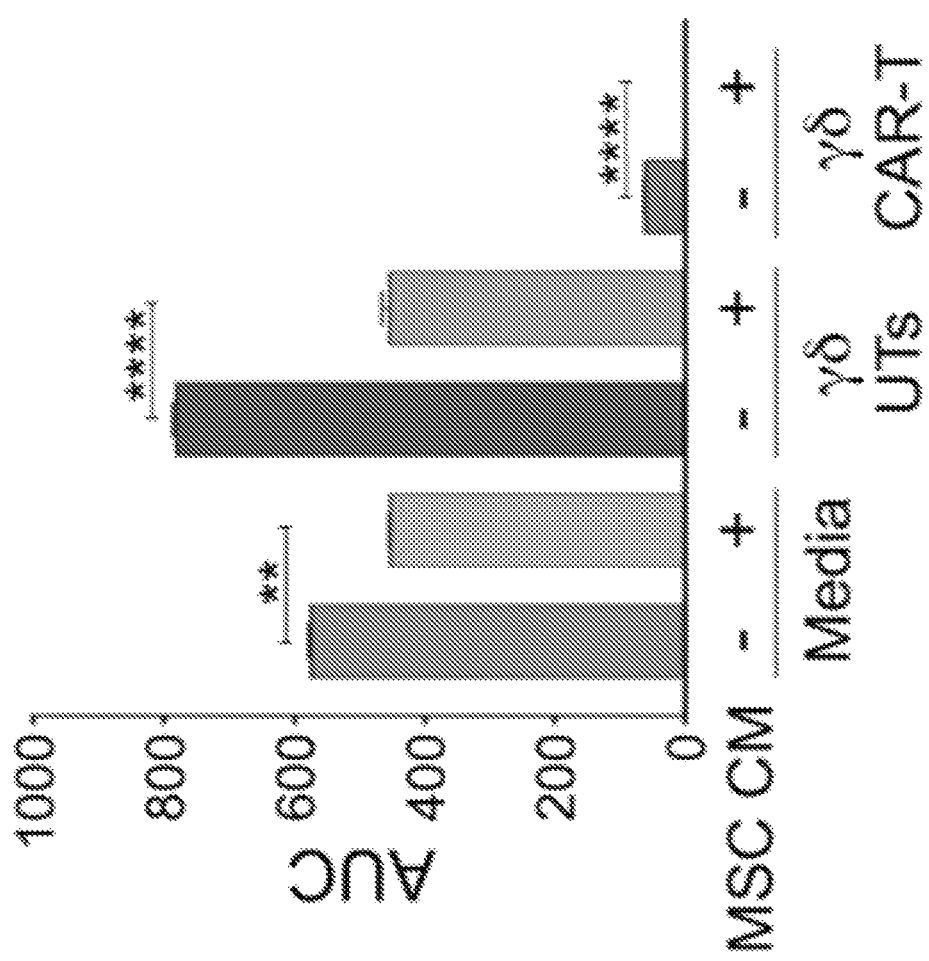

Bone marrow derived MSCs enhance the anti-C4-2B-PSCA efficacy of γδ CAR-T cells Mesenchymal stromal cells (MSCs) are commonly found in the bone and in bone mCRPC. In response to PCa-derived factors, MSCs can differentiate into osteoblasts, which are the key mediators of PCa-induced osteogenesis. While MSCs can regulate PCa behavior, the effects of MSCs on γδ T-cells and vice versa have not been characterized thus far in the context of bone mCRPC. Because of mixed reports of MSCs on T-cell behavior in the literature, the effect of human MSCs (Lonza Cat PT-2501) on γδ T-cell activity was initially examined. Using the impedance-based RTCA assay, it was found that the addition of MSC CM to γδ T-cells significantly enhanced rather than inhibited their activity (FIGS. 14A and 14B). C4-2B-PSCA cells were treated with untransduced (UT) or CAR-transduced γδ T-cells, in standard culture media, or in media supplemented with 50% MSC conditioned media (CM). CM decreased the viability of C4-2B-PSCA cells treated with γδ (CAR)-T cells (FIG. 14A). Notably, while tumor cells started to grow back after 2 days posttreatment with CAR-T cells alone, they remained undetectable after treatment with CAR-T cells plus CM. Changes in cumulative viability (AUC) were statistically significant (FIG. 14B). These data suggest autologous bone marrow MSCs may enhance the activity of γδ CAR-T cells.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of providing an anti-cancer immunity in a subject with a bone metastatic cancer, the method comprising
   a) administering to the subject an effective amount of a gamma-delta T cell stimulating agent; and
   b) administering to the subject an effective amount of a T cell expressing a gamma-delta T cell receptor (TCR) and a chimeric antigen receptor (CAR) polypeptide,
      wherein the CAR polypeptide comprises a single-chain variable fragment (scFv) of an antibody that specifically binds prostate stem cell antigen (PSCA) binding domain, a CD8-derived transmembrane domain, a CD28-derived co-stimulatory signaling region, and a CD32-derived activation domain.

2. The method of claim 1, wherein the gamma-delta T cell stimulating agent comprises a bisphosphonate.

3. The method of claim 2, wherein the bisphosphonate is selected from the group consisting of alendronate, clodronate, etidronate, pamidronate, tiludronate, ibandronate, zoledronate, olpadronate, residronate and neridronate.

4. The method of claim 1, further comprising administering to the subject a checkpoint inhibitor.

5. The method of claim 4, wherein the checkpoint inhibitor comprises an anti-PD-1 antibody, anti-PD-L1 antibody, anti-CTLA-4 antibody, or a combination thereof.

6. The method of claim 1, further comprising measuring T cells in the cancer after treatment, and adjusting the amount of gamma-delta T cell stimulating agent to achieve an effective amount of T cells in the cancer.

* * * * *